(12) United States Patent
Carroll et al.

(10) Patent No.: US 6,974,824 B2
(45) Date of Patent: Dec. 13, 2005

(54) KAPPA OPIOID RECEPTOR LIGANDS

(75) Inventors: F. Ivy Carroll, Durham, NC (US); James B. Thomas, Efland, NC (US); S. Wayne Mascarella, Hillsborough, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 440 days.

(21) Appl. No.: 09/755,021

(22) Filed: Jan. 8, 2001

(65) Prior Publication Data

US 2002/0132828 A1 Sep. 19, 2002

(51) Int. Cl.⁷ ............ A61K 31/445; C07D 251/00; C07D 401/00; C07D 217/00; C07D 487/00
(52) U.S. Cl. ............ 514/317; 514/241; 514/256; 514/291; 514/292; 514/293; 514/307; 514/311; 544/180; 544/333; 546/81; 546/82; 546/84; 546/139; 546/152; 540/577
(58) Field of Search ............... 514/317, 241, 514/256, 291–293, 307, 311; 544/180, 333; 546/81, 82, 84, 139, 152; 540/577

(56) References Cited

U.S. PATENT DOCUMENTS

| 5,767,131 A | * | 6/1998 | Gluchowski et al. | 514/318 |
| 6,159,990 A | * | 12/2000 | Lagu et al. | 514/326 |
| 6,218,390 B1 | * | 4/2001 | Lagu et al. | 514/237.5 |
| 6,268,369 B1 | * | 7/2001 | Nagarathnam et al. | 514/256 |
| 2002/0013321 A1 | | 1/2002 | Liras | 514/249 |
| 2004/0072865 A1 | * | 4/2004 | Bouillot et al. | 514/317 |

FOREIGN PATENT DOCUMENTS

EP 1 038 872 9/2000

* cited by examiner

*Primary Examiner*—James O. Wilson
*Assistant Examiner*—Tamthom N. Truong
(74) *Attorney, Agent, or Firm*—Oblon, Spivak, McClelland, Maier & Neustadt, P.C.

(57) ABSTRACT

Kappa opioid receptor antagonists are provided that yield significant improvements in functional binding assays to kappa opioid receptors relative to nor-BNI, and the use of these antagonists in treatment of disease states that are ameliorated by binding of the kappa opioid receptor such as heroin or cocaine addictions.

16 Claims, 4 Drawing Sheets

Figure 2

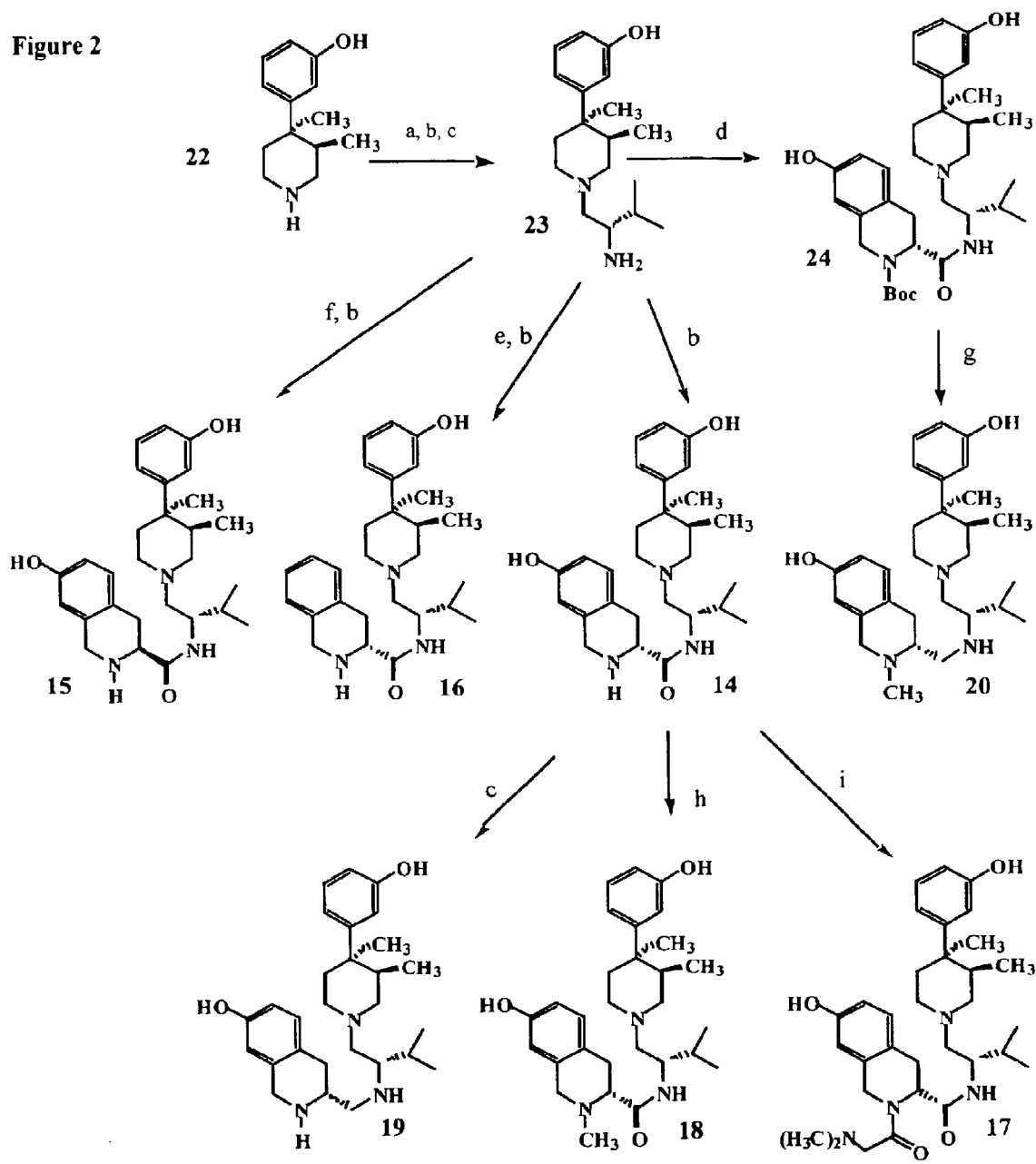

Reagents: (a) Boc-L-valine, BOP, TEA, THF; (b) TFA, CH2Cl2; (c) borane/dimethyl sulfide; (d) Boc-D-7-hydroxy-1,2,3,4-tetrahydroisoquinoline-3-carboxylic acid, BOP, TEA, THF; (e) Boc-D-1,2,3,4-tetrahydroisoquinoline-3-carboxylic acid, BOP, TEA, THF; (f) Boc-L-7-hydroxy-1,2,3,4-tetrahydroisoquinoline-3-carboxylic acid, BOP, TEA, THF; (g) Lithium aluminum hydride, THF; (h) formalin, NaBH(OAc)3, dichloroethane; (i) N,N-dimethylglycine, BOP, TEA, THF Reagents: (a) Boc-L-valine, BOP, TEA, THF; (b) TFA, CH2Cl2; (c) borane/dimethyl sulfide; (d) Boc-D-7-hydroxy-1,2,3,4-tetrahydroisoquinoline-3-carboxylic acid, BOP, TEA, THF

KAPPA OPIOID RECEPTOR LIGANDS

BACKGROUND OF THE INVENTION

1. Field of the Invention

The present invention relates to compounds that bind with high affinity and/or specificity to kappa opioid receptors.

2. Background of the Invention

The study of compounds exerting their actions via the opioid receptor system has continued for nearly eight decades. Though this has been a broad effort, the fundamental driving force for this endeavor relates to the elimination or reduction of the side-effect profile produced by the most frequently used or abused opiates morphine (1) and heroin (2) in FIG. 1. Among the many side effects produced by compounds 1 and 2, addiction, tolerance and respiratory depression are of greatest concern when heroin abuse is considered. Though its use waned in the late 70s, increases in both the purity and availability of this drug have promoted a serious resurgence of illegal use. In the study and treatment of substance abuse, antagonists for the opioid receptors like naltrexone (3) (FIG. 1) have played a prominent role. In recent years, researchers studying the physiological mechanisms underlying addiction have sought antagonists selective for each of the three opioid receptor subtypes mu, delta and kappa. Extensive research efforts along these lines lead to the discovery of several such compounds with examples including cyprodime (mu, 4), naltrindole (delta, 5) and nor-binaltorphimine (kappa, 6) (FIG. 1). Of the three, the kappa receptor has only begrudgingly yielded antagonists and, of the known examples, all stem from modification of the prototype, nor-binaltorphimine (nor-BNI, 6).

Portoghese in his pioneering work provided not only the second and third generation kappa antagonists 5'-[(N2-butylamidino)methyl]naltrindole (7) and C5'-guanidinylnaltrindole (GNTI, 8) but also convincing evidence that the Glu297 residue in transmembrane helix 6 of the kappa receptor is the principle address site influencing the kappa selectivity found in 6–8 (FIG. 1). In terms of the message address concept as applied by Portoghese to opioid small-molecules, it is the pendant amine functionality (noted by asterisks in the chart) present in 6–8 that functions as the kappa address element by interacting with the Glu297 residue which is present in the kappa but not in the mu receptor.

In terms of substance abuse treatment, antagonists selective for the kappa receptor have been the least studied primarily due to the limited bio-availability of 6 and its analogs. However, mounting evidence that the endogenous kappa opioid system opposes the actions of mu agonists like 2 suggests that antagonists selective for the kappa receptor system could suppress or eliminate the symptoms of withdrawal which arise from an overactive kappa receptor system and thus could promote abstinence and prevent relapse. Therefore, the development of novel kappa antagonists possessing improved pharmacokinetic profiles would be of great value.

As is obvious from the examples above, the morphinan substructure of 3 has served as the preeminent template upon which selective antagonists have been constructed. Contrary to these efforts, our work in this field started from the relatively unstudied N-substituted trans-(3,4)-dimethyl-4-(3-hydroxyphenyl)piperidine class of opioid antagonist discovered by Zimmerman et al. Compounds like 9a and 9b (FIG. 1) were novel opioid antagonists because their intrinsic antagonist activity was not mediated by the structure of their N-substituent (i.e. the N-methyl (9a) and N-cyclopropylmethyl (9b) analogs in the phenylpiperidine series are both pure antagonists). Indeed, no N-substituent has been discovered which converts this series of compound into an agonist. Compounds 10–12 (FIG. 1) represent some of the structures tried to date. In this connection we recently demonstrated that compounds bearing the trans-cinnamyl N-substituent, as found in 13 (FIG. 1), most closely reproduced the potency at the mu opioid receptor of the flexible N-substituted analogs (10–12). In fact, the comparable mu receptor potencies demonstrated by analogs trans-(3,4)-dimethyl-4-(3-hydroxyphenyl)piperidine possessing the trans-cinnamyl moiety lead us to speculate that in their biologically active conformation, compounds such as 10–12 have the connecting chain and appended ring in their N-substituent extended away from the piperidine nitrogen in a manner consistent with the trans-cinnamyl skeleton like that found in 13.

In more recent studies comparing opioid receptor potency and selectivity to N-substituent changes in this series of antagonists, we discovered 14–21 (FIG. 1). These compounds were obtained from the screening of libraries of compounds which were biased for opioid antagonist activity by incorporation of trans-(3,4)-dimethyl-4-(3-hydroxyphenyl)piperidine into each ligand. In biological testing those compounds (14–21) were found to possess kappa opioid receptor subtype selectivity in binding assays.

SUMMARY OF THE INVENTION

It is an object of the invention to provide compounds which bind to kappa opioid receptors with high affinity.

It is another object of the invention to provide compounds which bind to kappa opioid receptors with high specificity.

It is another object of the invention to provide compounds which bind to kappa opioid receptors with high affinity and specificity in functional assays.

The objects of the present invention, and others, are accomplished with compounds of the structures described herein, particularly compounds 14–21, which have the above advantages. To the inventors knowledge, compounds 14, 18, 19 and 20 have the highest affinity and selectivity for the kappa opioid receptor of any compounds yet reported (Table 1). Compound 14 was also studied in the [$^{35}$S]GTPγS functional assay, and in particular, maintained kappa selectivity between binding and functional assays and showed a $K_i$ value of 0.006 nM for the kappa receptor and a mu/kappa $K_i$ ratio of 570 (Table 3).

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 2: synthetic route to compounds (14–20);

DETAILED DESCRIPTION OF THE INVENTION

Figure 1:
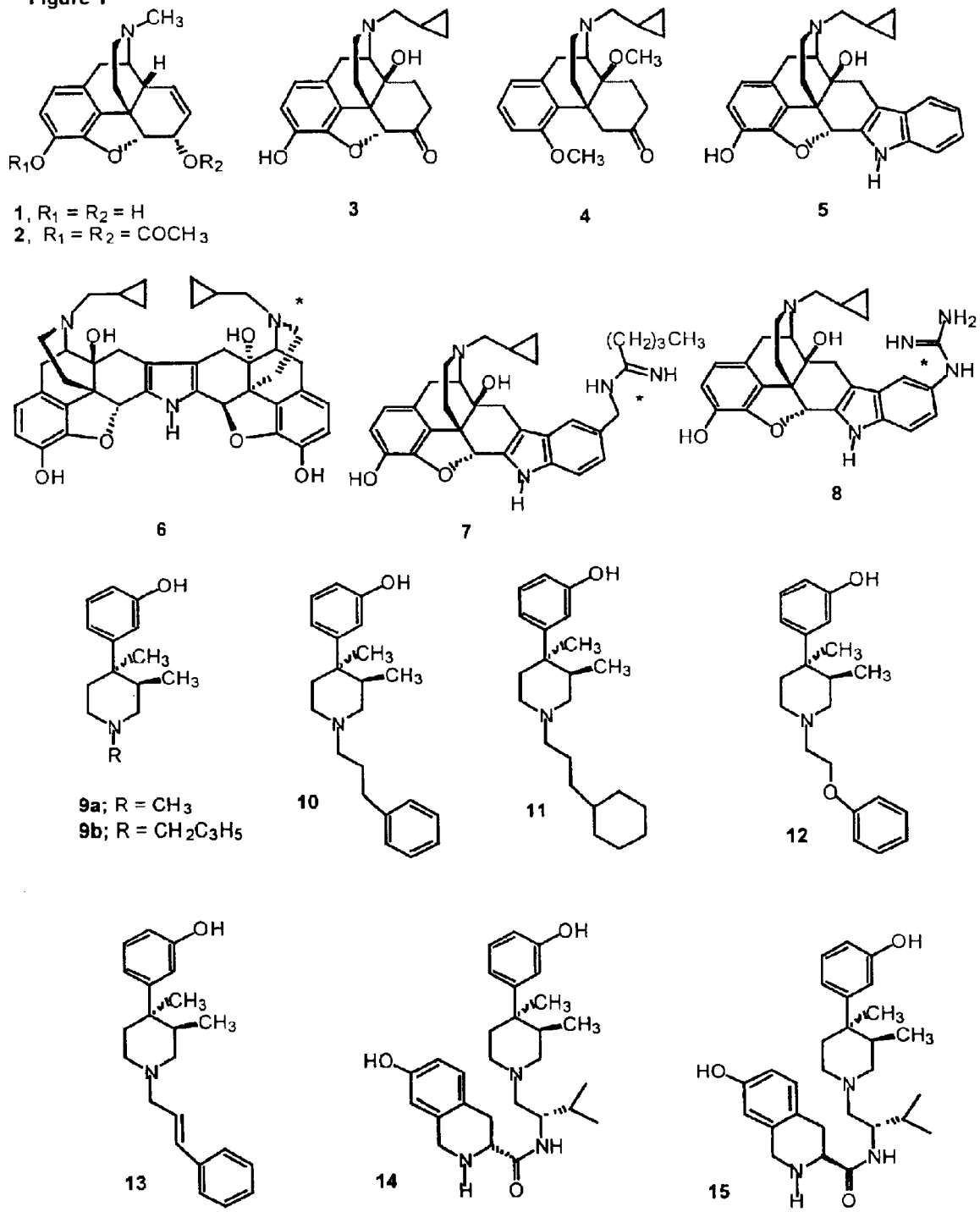
FIG. 1: chemical structure of compounds (1)–(21)
Figure 1:
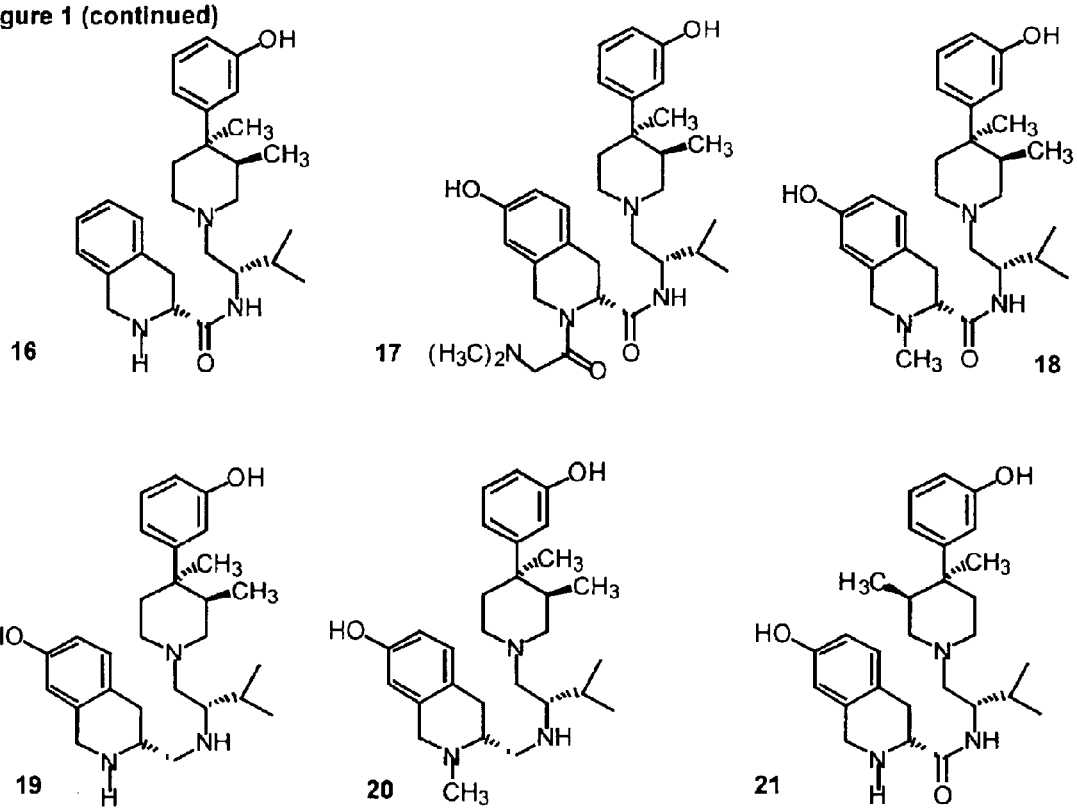

The present invention provides kappa opioid antagonists that bind to kappa opioid receptors with high affinity and/or specificity. Compounds of the present invention are those represented by the formula (I):

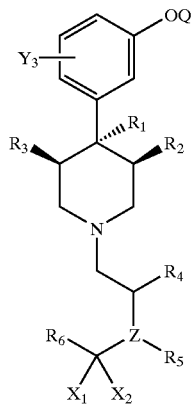
(I)

wherein Q is H or $COC_{1-8}$ alkyl;
$R_1$ is $C_{1-8}$ alkyl, or one of the following structures:

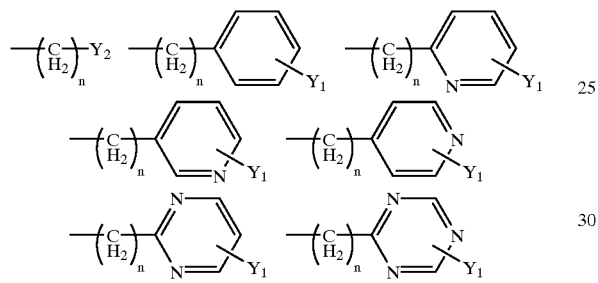

$Y_1$ is H, OH, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;

$Y_2$ is H, $CF_3$, $CO_2R_9$, $C_{1-6}$alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H, OH, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;

$R_2$ is H, $C_{1-8}$ alkyl, $C_{3-8}$ alkenyl, $C_{3-8}$ alkynyl or $CH_2$aryl substituted by one or more groups $Y_1$;

$R_3$ is H, $C_{1-8}$ alkyl, $C_{3-8}$ alkenyl, $C_{3-8}$ alkynyl or $CH_2$aryl substituted by one or more groups $Y_1$;

wherein $R_2$ and $R_3$ may be bonded together to form a $C_{2-8}$ alkyl group;

$R_4$ is hydrogen, $C_{1-8}$ alkyl, $CO_2C_{1-8}$ alkylaryl substituted by one or more groups $Y_1$, $CH_2$aryl substituted by one or more groups $Y_1$ or $CO_2C_{1-8}$ alkyl;

Z is N, O or S; when Z is O or S, there is no $R_5$ $R_5$ is H, $C_{1-8}$ alkyl, $C_{3-8}$ alkenyl, $C_{3-8}$ alkynyl, $CH_2CO_2C_{1-8}$ alkyl, $CO_2C_{1-8}$ alkyl or $CH_2$aryl substituted by one or more groups $Y_1$; (when Z is O or S, there is no $R_5$)

n is 0, 1, 2 or 3;

$R_6$ is a group selected from the group consisting of structures (a)–(bbb):

(a)
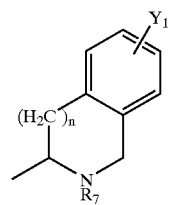

(b)
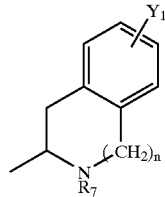

(c)
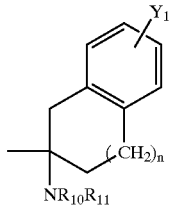

(d)
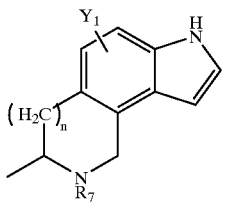

(e)
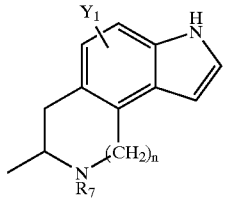

(f)
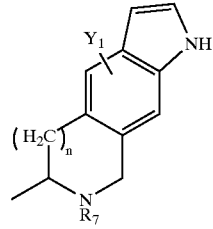

(g)
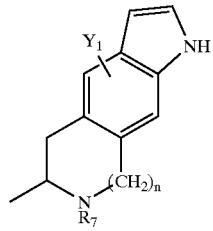

(h)
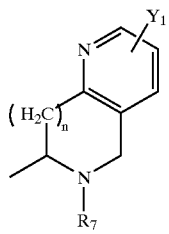

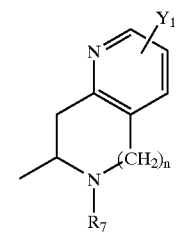
(i)
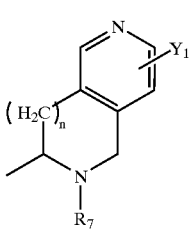
(j)
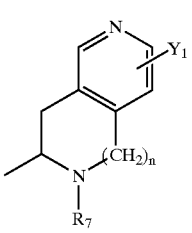
(k)
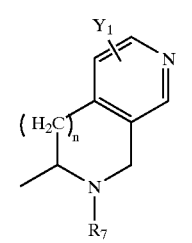
(l)
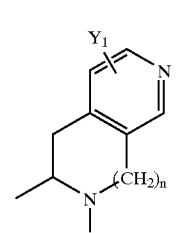
(m)
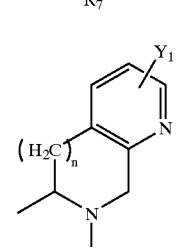
(n)
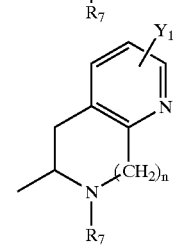
(o)
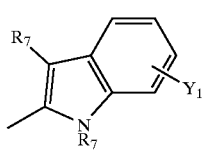
(p)
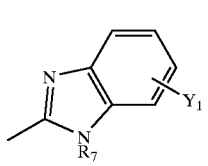
(q)
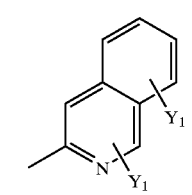
(r)
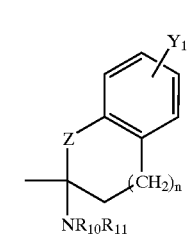
(s)
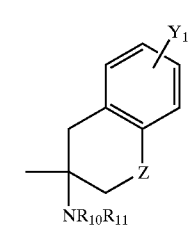
(t)
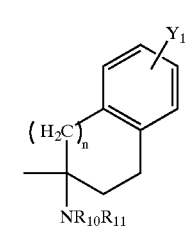
(u)
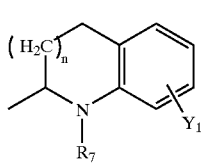
(v)
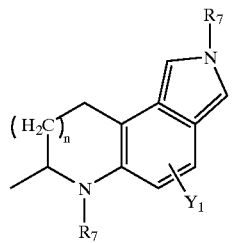
(w)

-continued
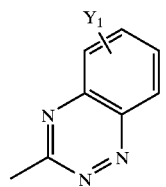 (x)
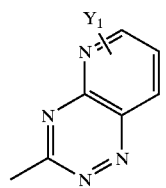 (y)
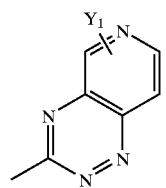 (z)
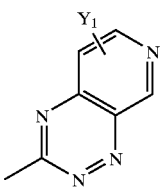 (aa)
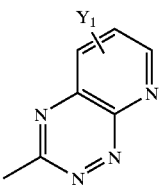 (bb)
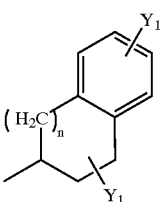 (cc)
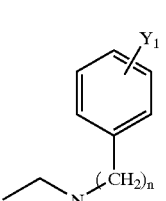 (dd)
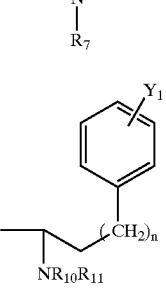 (ee)
-continued
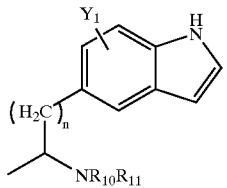 (ff)
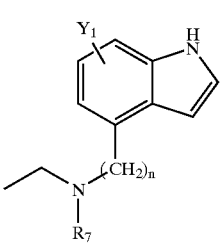 (gg)
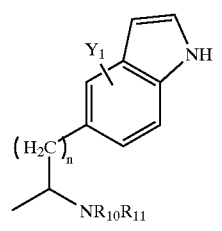 (hh)
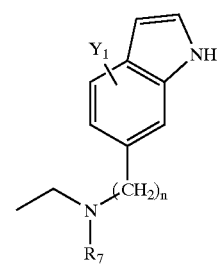 (ii)
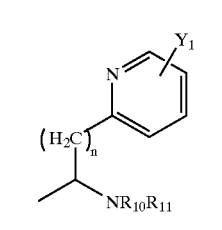 (jj)
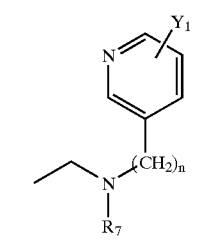 (kk)
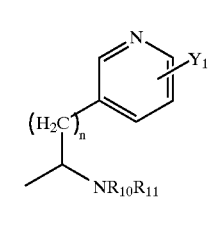 (ll)

-continued (mm)

(nn)

(oo)

(pp)

(qq)

(rr)

(ss)

(tt)

-continued (uu)

(vv)

(ww)

(xx)

(yy)

(zz)

(aaa)

(bbb)

$X_1$ is hydrogen, $C_{1-8}$ alkyl, $C_{3-8}$alkenyl, or $C_{3-8}$alkynyl;

$X_2$ is hydrogen, $C_{1-8}$alkyl, $C_{3-8}$alkenyl, or $C_{3-8}$alkynyl; or $X_1$ and $X_2$ together form $=O$, $=S$, or $=NH$;

$R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, $CH_2(CH_2)_nY_2$, or $C(=NH)NR_{16}R_{17}$;

$R_8$ is H, $C_{1-8}$alkyl, $CH_2$aryl substituted by one or more substituents $Y_1$, $CONR_{13}R_{14}$, or $CH_2(CH_2)_nY_2$;

$R_9$ is H, $C_{1-8}$ alkyl, $CH_2$ aryl substituted by one or more substituents $Y_1$, or $CH_2(CH_2)_nY_2$;

$R_{10}$ is H, $C_{1-8}$ alkyl, $CH_2$ aryl substituted by one or more substituents $Y_1$, or $CH_2(CH_2)_nY_2$;

$R_{11}$ is H, $C_{1-8}$ alkyl, $CH_2$ aryl substituted by one or more substituents $Y_1$, or $CH_2(CH_2)_nY_2$;

$R_{12}$ is H, $C_{1-8}$ alkyl, $CH_2$ aryl substituted by one or more substituents $Y_1$, or $CH_2(CH_2)_nY_2$;

$R_{13}$ is H, $C_{1-8}$ alkyl, $CH_2$ aryl substituted by one or more substituents $Y_1$, or $CH_2(CH_2)_nY_2$;

$R_{14}$ is H, $C_{1-8}$ alkyl, $CH_2$ aryl substituted by one or more substituents $Y_1$, or $CH_2(CH_2)_nY_2$;

$R_{15}$ is H, $C_{1-8}$ alkyl, $CH_2$ aryl substituted by one or more substituents $Y_1$, or $CH_2(CH_2)_nY_2$;

$R_{16}$ is H, $C_{1-8}$ alkyl, $CH_2$ aryl substituted by one or more substituents $Y_1$, or $CH_2(CH_2)_nY_2$; and $R_{17}$ is H, $C_{1-8}$ alkyl, $CH_2$ aryl substituted by one or more substituents $Y_1$, or $CH_2(CH_2)_nY_2$.

Preferably, the compounds of the present invention are those represented by the formula I as shown above, wherein $R_1$, $R_4$, $R_5$, $Y_1$, $Y_2$, Z, n, $X_1$, $X_2$, and $R_7$–$R_{17}$ are as indicated above;

$Y_3$ is H;

$R_2$ and $R_3$ are each, independently, H, $C_{1-8}$ alkyl, $C_{3-8}$ alkenyl, $C_{3-8}$ alkynyl, or $CH_2$aryl substituted by one or more substituents $Y_1$; and $R_6$ is a group having a formula selected from the group consisting of structures (a)–(cc) above.

More preferably, the compounds of the present invention are those represented by the formula I as shown above, wherein $Y_1$, $Y_2$, $R_4$, $R_5$, Z, n, $X_1$, $X_2$ and $R_8$–$R_{15}$ are as indicated above;

$R_1$ is $C_{1-8}$ alkyl,

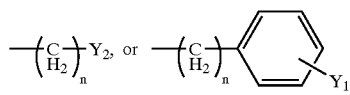

$Y_3$ is H;

$R_2$ and $R_3$ are each, independently, H or $C_{1-8}$ alkyl, wherein $R_2$ and $R_3$ cannot both be H at the same time;

$R_6$ is a formula selected from the structures (a)–(r) shown above; and $R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

Still more preferably, the compound of the present invention are those represented by the formula I as shown above, wherein $Y_1$, Z, n, $X_1$, $X_2$ and $R_8$–$R_{15}$ are as noted above;

$R_1$ is $C_{1-8}$ alkyl;

$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_{3,\ or\ COCH2}R_9$;

$Y_3$ is H;

$R_2$ and $R_3$ are each, independently, H or methyl, wherein $R_2$ and $R_3$ cannot both be H at the same time;

$R_4$ is H, $C_{1-8}$ alkyl, $CO_2C_{1-8}$alkyl, aryl substituted by one or more substituents $Y_1$ and the stereocenter adjacent to $R_4$ is in an (S) configuration;

$R_5$ is H, $C_{1-8}$ alkyl, or $CH_2CO_2C_{1-8}$ alkyl;

$R_6$ is a group having a formula selected from the group consisting of structures (a)–(c) and (h)–(o);

$R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

Most preferably, the compounds of the present invention are those represented by the formula I as shown above, wherein $Y_1$, Z, n, $X_1$, $X_2$ and $R_8$–$R_{14}$ are as indicated above;

$R_1$ is methyl, $Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each H or methyl, such that when $R_2$ is H, $R_3$ is methyl and vice versa;

$R_4$ is $C_{1-8}$ alkyl, or $CO_2C_{1-8}$ alkyl, and the stereocenter adjacent to $R_4$ has a configuration of (S);

$R_5$ is H;

$R_6$ is a group having a formula selected from the group consisting of structures (a) and (b); and $R_7$ is H, $C_{1-8}$ alkyl, $CH_2$aryl substituted by one or more substituents $Y_1$ or $CH_2(CH_2)_nY_2$.

A most preferred set of compounds are the compounds of formula 14–21 as shown in FIG. 1.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom.

The aryl group is a hydrocarbon aryl group, such as a phenyl, naphthyl, phenanthryl, anthracenyl group, which may have one or more $C_{1-4}$ alkyl group substituents.

The compounds of the present invention are opiates which are preferably antagonists that are selective for the kappa receptor. The $\kappa/\mu$ selectivity may be at least 2:1, but is preferably higher, e.g., at least 5:1, 10:1, 25:1, 50:1, 100:1, 200:1 or even 500:1. The $\kappa/\delta$ selectivity may be at least 2:1, but is preferably higher, e.g., at least 5:1, 10:1, 25:1, 50:1, 100:1, 200:1, 250:1, 500:1 or even 1000:1.

Figure 3:
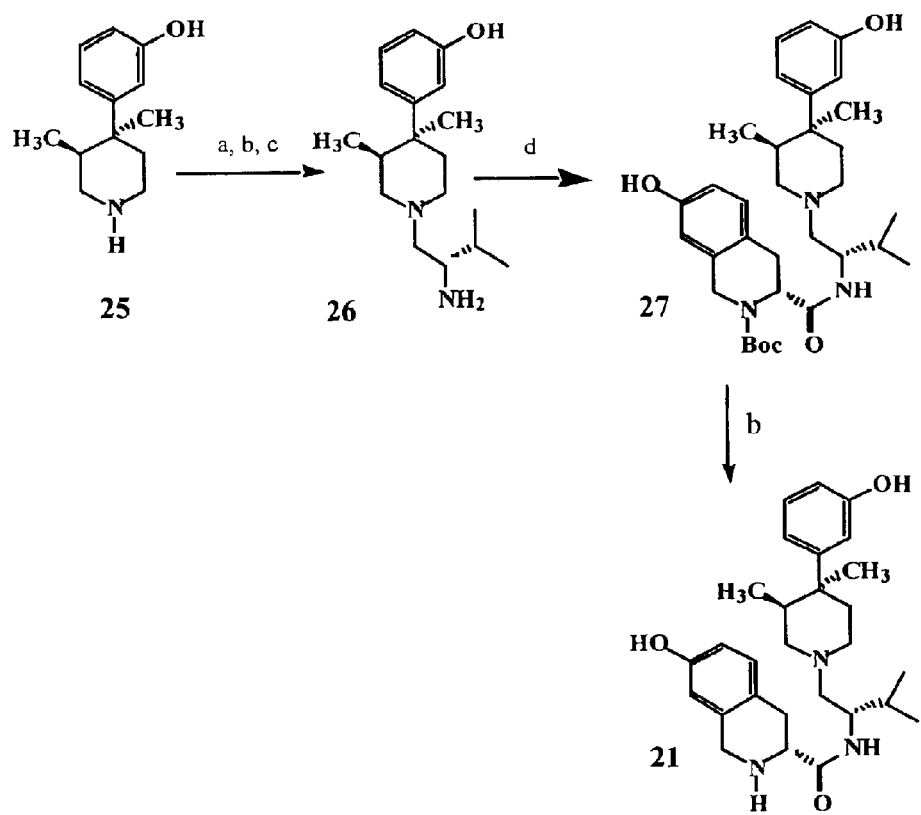
FIG. 3: synthetic route to compound 21.

The compounds of the present invention may be synthesized, for example, in accordance with the reaction sequence shown in FIG. 2 and FIG. 3.

The compounds of the present invention may be in the form of a pharmaceutically acceptable salt via protonation of the amines with a suitable acid. The acid may be an inorganic acid or an organic acid. Suitable acids include, for example, hydrochloric, hydroiodic, hydrobromic, sulfuric, phosphoric, citric, acetic, fumaric and formic acids.

The receptor selectivities discussed above are determined based on the binding affinities at the receptors indicated or their selectivity in opioid functional assays.

The compounds of the present invention may be used to bind opioid receptors. Such binding may be accomplished by contacting the receptor with an effective amount of the inventive compound. Of course, such contacting is preferably conducted in an aqueous medium, preferably at physiologically relevant ionic strength, pH, etc.

The inventive compounds may also be used to treat patients having disease states which are ameliorated by binding opioid receptors or in any treatment wherein temporary suppression of the kappa opioid receptor system is desired. Such diseases states include opiate addiction (such as heroin addiction), or cocaine addiction. The compounds of the present invention may also be used as cytostatic agents, as antimigraine agents, as immunomodulators, as immunosuppressives, as antiarthritic agents, as antiallergic agents, as virucides, to treat diarrhea, as antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anticonvulsants, or to treat obesity. Additionally, the present compounds can be used in the treatment of Parkinson's disease as an adjunct to L-dopa for treatment of dyskinesia associated with the L-dopa treatment.

The compounds may be administered in an effective amount by any of the conventional techniques well-established in the medical field. For example, the compounds may be administered orally, intraveneously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480–590, incorporated herein by reference. The patient is preferably a mammal, with human patients especially preferred. Effective amounts are readily determined by those of ordinary skill in the art. Studies by the present inventors show no toxicity and no lethality for the present compounds at amounts up to 300 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2–4 equal doses per day.

Suitable compositions containing the present compounds further comprise a physiologically acceptable carrier, such as water or conventional pharmaceutical solid carriers, and if desired, one or more buffers and other excipients.

EXAMPLES

Having generally described this invention, a further understanding can be obtained by reference to certain specific examples which are provided herein for purposes of illustration only and are not intended to be limiting unless otherwise specified.

Chemistry

Coupling of (3R,4R)-dimethyl-4-(3-hydroxyphenyl) piperidine (22) with tert-butoxy-carbonyl-protected L-valine (Boc-protected) using benzotriazol-1-yl-oxy-tris-(dimethylamino)phosphonium hexafluorophosphate (BOP reagent) in THF and removal of the Boc-protecting group with trifluoroacetic acid (TFA) in methylene chloride followed by reduction using a tetrahydrofuran (THF) solution of borane-dimethyl sulfide complex gave the intermediate amine 3-[1-(2S-Amino-3-methylbutyl)-3R,4R-dimethyl-4-piperidinyl]phenol (23) in 74% yield (FIG. 2). From this versatile intermediate was derived (3R)-7-Hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide(14), (3S)-7-Hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide(15), and (3R)-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide(16) by first coupling with either Boc-D-7-hydroxy-1,2,3,4-tetrahydroisoquinoline-3-carboxylic acid (for 14), Boc-L-7-hydroxy-1,2,3,4-tetrahydroisoquinoline-3-carboxylic acid (for 15) or Boc-D-1,2,3,4-tetrahydroisoquinoline-3-carboxylic acid (for 16) respectively followed by removal of the Boc protecting groups with TFA as previously described. Treatment of intermediate compound tert-butyl-(3R)-7-hydroxy-3-{[((1S)-1-{[(3R,4R)-4-(3-hydroxyphenyl)-3,4-dimethyl-1-piperidinyl]methyl}-2-methylpropyl)amino]carbonyl}-3,4-dihydrohydro-2(1H)-isoquinolinecarboxylate (24) with lithium aluminum hydride in refluxing THF followed by a basic work-up gave (3R)-3-{[((1S)-1-{[(3R,4R)-4-(3-hydroxyphenyl)-3,4-dimethyl-1-piperidinyl]methyl}-2-methylpropyl)amino]methyl}-2-methyl-1,2,3,4-tetrahydro-7-isoquinolinol(20). Compounds (3R)-2-(N,N-dimethylglycyl)-7-hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (17), (3S)-7-Hydroxy-N-((1S)-1-{[(3R,4R)-4-(3-hydroxyphenyl)-3,4-dimethyl-1-piperidinyl]methyl}-2-methylpropyl)-2-methyl-1,2,3,4-tetrahydro-3-isoquinolinecarboxamide(18) and (3R)-3-{[((1S)-1-{[(3R,4R)-4-(3-hydroxyphenyl)-3,4-dimethyl-1-piperidinyl]methyl}-2-methylpropyl)amino]methyl}-1,2,3,4-tetrahydro-7-isoquinolinol (19) were each derived from (3R)-7-Hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide(14) by different synthetic routes. For example, compound 19 was prepared by reducing 14 with borane in THF as previously described. Compound 18 was prepared by treating 14 with formalin and sodium triacetoxyborohydride followed by a basic work-up. Compound 17 was prepared from 14 via a BOP mediated coupling with N,N-dimethylglycine. As shown in FIG. 3, compound (3R)-7-Hydroxy-N-((1S)-1-{[(3S,4S)-4-(3-hydroxyphenyl)-3,4-dimethyl-1-piperidinyl]methyl}-2-methylpropyl)-1,2,3,4-tetrahydro-3-isoquinolinecarboxamide (21) was prepared according to the same synthetic route used to obtain 14. Thus, coupling (−)-(3S,4S)-dimethyl-4-(3-hydroxyphenyl)piperidine (25) with tert-butoxycarbonyl-protected L-valine using BOP reagent in THF and removal of the Boc-protecting group with TFA followed by borane reduction gave the intermediate amine 3-[1-(2S-Amino-3-methylbutyl)-3S,4S-dimethyl-4-piperidinyl]phenol (26). Coupling with Boc-D-7-hydroxy-1,2,3,4-tetrahydroisoquinoline-3-carboxylic acid gave tert-butyl-(3R)-7-hydroxy-3-{[((1S)-1-{[(3S,4S)-4-(3-hydroxyphenyl)-3,4-dimethyl-1-piperidinyl]methyl}-2-methylpropyl)amino]carbonyl}-3,4-dihydrohydro-2(1H)-isoquinolinecarboxylate (27) which then provided (3R)-7-hydroxy-N-((1S)-1-{[(3S,4S)-4-(3-hydroxyphenyl)-3,4-dimethyl-1-piperidinyl]methyl}-2-methylpropyl)-1,2,3,4-tetrahydro-3-isoquinolinecarboxamide (21) following removal of the Boc protecting group with TFA as previously described.

Biological

The binding affinities of the novel kappa antagonists 14–21, and the standard kappa antagonist nor-BNI (6) at the mu, delta, and kappa opioid receptors were determined using competitive binding assays following previously reported procedures, Table 1. Measures of antagonism were obtained by monitoring selected test compounds ability to inhibit stimulation of [$^{35}$S]GTP-γ-S binding produced by the selective agonists (D-Ala$^2$, MePhe$^4$, Gly-ol$^5$)enkephalin (DAMGO, mu receptor), (+)-4[(αR)-α-(2S,5R)-4-allyl-2,5-dimethyl-1-piperazinyl)-3-methoxybenzyl]-N,N-diethylbenzamide (SNC-80, delta) and 5α,7α, 8β-(−)-N-methyl-N-[7-(1-pyrrolidinyl)-1-oxaspiro[4,5]dec-8-yl] benzeneacetamide (U69,593, kappa) in guinea pig caudate (Table 2) and in cloned human receptors, Table 3.

Results and Discussion

Inspection of the binding data in Table 1 for the standard antagonist nor-BNI (6) indicates that it has far higher affinity for the kappa receptor ($K_i$=1.09) relative to either the mu receptor ($K_i$=65) or the delta receptor ($K_i$=86). Thus in this assay, the standard kappa antagonist behaves as expected with a 60-fold selectivity for the kappa versus the mu receptor and a 79-fold selectivity for the kappa versus the delta receptor. Comparison of the data for the novel compounds 14–21 reveals that all of these compounds possesses superior delta/kappa selectivity relative to 6 and many possess superior mu/kappa selectivity. In terms of binding affinity to the kappa receptor, many of the novel compounds, for example, 14 and 18–20 possess far greater affinity than the standard kappa antagonist nor-BNI (6). Moreover, 18–20 are much more selective for the kappa receptor relative to the mu and delta. With a $K_i$ value of 2.1 nM at the kappa receptor, compound 16 is slightly less potent than nor-BNI (6); however, it also is much more selective for the kappa receptor. Compounds 15 and 21, which are diastereoisomers of 14, possess weaker affinity for the kappa receptor and or less selectivity. These findings show the novelty of 14 and its analogs.

In a functional assay using guinea pig membranes (Table 2), the standard antagonist nor-BNI (6) shows a 28-fold increase in its $K_i$ relative to that seen in the binding assay. At the mu and delta receptors however, the $K_i$s for 6 of 16.7 nM and 10.2 nM represent only 4 and 8.5-fold increases respectively. Overall this translates into a significant increase in mu versus kappa and delta versus kappa selectivity in this assay relative to its performance in the binding assay. The novel compound 14 also shows an improvement in its $K_i$ for the kappa receptor in this assay relative to the binding assay ($K_i$=0.02 nM). Coupled to the observation that the $K_i$ for compound (14) at either the mu or delta receptors do not increase substantially, results in greater than 100-fold mu versus kappa selectivity and an unprecedented >15,000-fold selectivity for the delta versus kappa receptor.

In the more relevant functional assay using cloned human opioid receptors, the novel antagonist 14 demonstrates a 3.4-fold increase in kappa receptor affinity relative to the functional assay utilizing guinea pig membranes. This represents an overall 53-fold improvement in kappa receptor $K_i$ compared with the binding assay and as before there is little shift in $K_i$ for either the mu or delta receptors. This effectively boosts the selectivities of compound 14 to 570 and >16,000-fold for mu versus kappa and delta versus kappa respectively. In this assay then, the novel antagonist 14 is observed to be both more selective and more potent than the standard antagonist nor-BNI (6) which shows mu versus kappa and delta versus kappa selectivity of only 225 and 172-fold respectively. Accordingly, compound 14 is, in this assay, the most potent and kappa opioid receptor selective antagonist yet identified.

Conclusions

The opioid receptor binding data for compounds 14–21 showed novel and unexpected high affinity and selectivity for the kappa opioid receptor. For example, compound 18, which possesses a completely different structure than nor-BNI, is 20-fold more potent than the reference compound nor-BNI (6) and possesses much greater selectivity. More important, comparison of 14 to nor-BNI in two functional assays shows that this novel class of kappa antagonists also exhibits an even greater degree of unexpected high affinity and selectivity for the kappa receptor in these assays. The novel structures of compounds 14–21 and the unexpected high affinity and selectivity demonstrated by this new class of compounds for the kappa receptor are sufficient to warrant the definition of 14 and its analogs as prototypic structures that could be used for the design of additional potent and selective kappa antagonists.

TABLE 1

Radioligand Binding Results at the Mu, Delta, and Kappa Opioid Receptors for Standard Compound nor-BNI (6) and the Novel Kappa Antagonists 14–21.

| | $K_i$ (nM ± SD) | | | | |
|---|---|---|---|---|---|
| Compound | μ [$^3$H]DAMGO[a] | δ [$^3$H]DADLE[b] | κ [$^3$H]U69,593[c] | μ/κ | δ/κ |
| 6, nor-BNI | 65.06 ± 5.6 | 86 ± 7.3 | 1.09 ± 0.14 | 60 | 79 |
| 14 | 3.73 ± 0.17 | 301 ± 50 | 0.32 ± 0.05 | 12 | 940 |
| 15 | 596 ± 29 | >4900 | 9.8 ± 1.6 | 61 | 500 |
| 16 | 775 ± 75 | >4900 | 2.1 ± 0.17 | 369 | >2333 |
| 17 | 164 ± 10.5 | >3400 | 15 ± 1.2 | 11 | >219 |
| 18 | 37 ± 1.4 | 616 ± 59 | 0.053 ± 003 | 700 | 11622 |
| 19 | 107 ± 11 | 5572 ± 713 | 0.63 ± 0.05 | 170 | 8844 |
| 20 | 59 ± 2.5 | 2231 ± 187 | 0.55 ± 0.04 | 107 | 4056 |
| 21 | 138 ± 8 | 144 ± 15 | 17.5 ± 2.5 | 7.8 | 8.2 |

[a][$^3$H]DAMGO [(D-Ala$^2$,MePhe$^4$,Gly-ol$^5$)enkephalin]. Tritiated ligand selective for μ opioid receptor.
[b][$^3$H]DADLE [(D-Ala$^2$,D-Leu$^5$)enkephalin]. Tritiated ligand selective for δ opioid receptor.
[c][$^3$H]U69,593 {[$^3$H](5α,7α,8β)-(−)-N-methyl-N-[7-(1-pyrrolidinyl)-1-oxaspiro[4,5]dec-8-yl]benzeneacetamide}. Tritiated ligand selective for κ opioid receptor.

TABLE 2

Inhibition by Antagonists of [$^{35}$S]GTP-γ-S Binding in Guinea Pig Caudate Stimulated by the Opioid Receptor Subtype-Selective Agonists, DAMGO (μ), SNC80 (δ), and U69,593 (κ).

| Compound | Apparent Functional $K_i$ (nM ± SD) | | | μ/κ | δ/κ |
|---|---|---|---|---|---|
| | μ DAMGO[a] | δ DADLE[b] | κ U69,593[c] | | |
| 6,nor-BNI | 16.7 ± 1.5 | 10.2 ± 1.0 | 0.038 ± 0.005 | 439 | 268 |
| 14 | 2.16 ± 0.75 | >300 | 0.02 ± .002 | 108 | >15,000 |

[a]DAMGO [(D-Ala$^2$,MePhe$^4$,Gly-ol$^5$)enkephalin]. Agonist selective for mu opioid receptor.
[b]SNC-80 ([(+)-4-[αR)-α-(2S,5R)-4-allyl-2,5-dimethyl-l-piperazinyl)-3-methoxybenzyl]-N,N-diethylbenzamide). Agonist selective for delta opioid receptor.
[c]U69,593 [(5α,7α,8α)-(-)-N-methyl-N-[7-(1-pyrrolidinyl)-l-oxaspiro[4,5]dec-8-yl]benzeneacetamide]. Agonist selective for kappa opioid receptor.

TABLE 3

Inhibition by Antagonists of [$^{35}$S]GTP-γ-S Binding in Cloned Human Opioid Receptors Stimulated by DAMGO (μ), SNS-80 (δ) and U69,593 (κ) Selective Opioid Agonists.

| Compound | Apparent Functional $K_i$ (nM ± SD) | | | μ/κ | δ/κ |
|---|---|---|---|---|---|
| | μ DAMGO[a] | δ DADLE[b] | κ U69,593[c] | | |
| 6,nor-BNI | 15.8 ± 5.7 | 12.1 ± 3.1 | 0.07 ± 0.03 | 225 | 172 |
| 14 | 3.42 ± 0.83 | >100 | 0.006 ± .001 | 570 | >16,667 |

[a]DAMGO [(D-Ala$^2$,MePhe$^4$,Gly-ol$^5$)enkephalin] is an agonist selective for mu opioid receptor. The apparent functional $K_i$ is the concentration of each compound required to produce a 50% attenuation of DAMGO (10 μm)-stimulated [$^{35}$S]GTP-γ-S binding.
[b]SNC-80 ([(+)-4-[(ocR)-oc-(2S,5R)-4-allyl-2,5-dimethyl-l-piperazinyl)-3-methoxybenzyl]-N,Ndiethylbenzamide) is an agonist selective for delta opioid receptor. The apparent functional concentration of each compound required to produce a 50% attenuation of SNC80 (10 μM)-stimulated [$^{35}$S]GTP-γ-S binding.
[c]U69,593 [(5 α,7α,8β)-(-)-N-methyl-N-[7-(I-pyrrolidinyl)-l-oxaspiro[4,5]dec-8-yl]benzeneacetamide]. Agonist selective for kappa opioid receptor. The apparent functional concentration of each compound required to produce a 50% attenuation of U69,593 (10 μM)stimulated [$^{35}$S]GTP-γ-S binding.

Experimental

3-[1-(2S-Amino-3-methylbutyl)-3R,4R-dimethyl-4-piperidinyl]phenol (23). (+)-(3R,4R)Dimethyl-4-(3-hydroxyphenyl)piperidine (22) (11.5 mmol), tert-butoxycarbonyl-protected L-valine (11.5 mmol) and BOP reagent (I 1.5 mmol) were combined in THF (150 mL) at room temperature, and to this was immediately added triethylamine (TEA) or diisopropylethylamine (25.3 mmol). After stirring for 1 h, the reaction mixture was poured into ethyl ether (500 mL) and water (150 mL) in a separatory funnel. The mixture was shaken and the aqueous layer removed. This procedure was repeated using 150 mL saturated NaHCO$_3$ and 150 mL brine. The organic layer was diluted with hexane until cloudy and dried (Na$_2$SO$_4$), concentrated under reduced pressure, then dissolved in 100 mL chloroform (stored over K$_2$CO$_3$), and concentrated again. This was placed on a high vacuum system to remove residual solvent yielding a foamy yellow/white solid.

After remaining under vacuum on the pump overnight, this unpurified material was dissolved in methylene chloride 45 mL and cooled to −20° C. (methanol/ice). To this was added neat trifluoroacetic acid in 10-mL portions over 2 min to give a total addition of 30 mL. The entire mixture was stirred for exactly 30 min and then the cooling bath was removed for exactly 30 min. At this point, the reaction mixture was poured into a 1 L beaker containing a large stir bar and a rapidly agitated mixture of saturated bicarbonate solution (400 mL) and chloroform (150 mL). After completed addition, the pH of the mixture was verified to be 10 and adjusted with solid sodium bicarbonate if necessary. This mixture was poured into a separatory funnel. Any precipitated organic compounds were rinsed into the separatory funnel using a small amount of methanol. The beaker was then rinsed with a small amount of water which was added to the separatory funnel. The layers were agitated, separated, and the aqueous layer extracted five additional times using 3:1 methylene chloride:THF. The combined organic layers were dried over sodium sulfate and the solvent removed at reduced pressure. The material was then placed on a high vacuum pump to yield a yellow foamy solid.

Unpurified material from the deprotection step was dissolved in THF (150 mL) and cooled to −20° C. (methanol/ice). To this stirred mixture was added a solution of borane dimethylsulfide complex, 2M in THF (150 m-mol) dropwise. The solution was then heated to reflux and held for 3 h after which time, the solution was cooled to −20° C., and to this was carefully added methanol (72 mL) dropwise. This mixture was stirred for 1 h at room temperature, 16.4 mL of 1M HCl in ethyl ether was added, the solution was allowed to stir for 30 min, and the solvents removed on a rotary evaporator. The resulting residue was partitioned between 3:1 methylene chloride:tetrahydrofuran and water, the pH was adjusted to 10 with saturated sodium bicarbonate, and the aqueous layer was saturated with sodium chloride and extracted several times with 3:1 methylene chloride:tetrahydrofuran. The combined organic layers were dried over sodium sulfate and the solvent removed. This material was purified by flash chromatography on a silica gel column which was prepared by slurry packing with chloroform. The impure compound was loaded on the column as a chloroform solution. Elution proceeded with neat chloroform followed by 3% methanol up to 10% methanol in chloroform as needed to elute the desired compounds. Product fractions were combined and the solvent was removed on a rotary evaporator. This material was dissolved in a minimum of hot ethyl acetate and allowed to crystallize. Crystalline material was isolated by filtration followed by washing with a small amount of ice-cold ethyl acetate and used directly in the next step after drying overnight in a vacuum oven. $^1$H NMR (MeOH-d$_4$) δ 7.126–7.062 (t, 1H), 6.769–6.735 (m, 2H), 6.603–6.558 (m, 1H), 2.657–2.179 (m, 8H), 2.000 (brs, 1H), 1.583–1.502 (m, 2H), 1.294 (s, 3H), 0.978–0.912 (q, 6H), 0.789–0.761 (d, 3H); $^{13}$C NMR (MeOH-d$_4$) δ 158.5, 153.3, 130.1, 117.8, 113.8, 113.3, 63.4, 55.8, 54.1, 53.3, 40.0, 39.5, 33.1, 31.9, 28.1, 19.6, 19.2, 16.8. MS (electrospray) M+1=29 1. Calculated=291.

Tert-butyl-(3R)-7-Hydroxy-3-{[((1S)-1-{[(3R,4R)-4-(3-hydroxyphenyl)-3,4-dimethyl-1-piperidinyl]methyl)-2-methylpropyl)amino]carbonyl}-3,4-dihydrohydro-2(1H)-isoquinolinecarboxylate (24). Solid BOP reagent (1.65 g, 3.75 mmol) was added to a solution of 23 (0.943 g, 3.25 mmol), Boc-D-7-hydroxy-1,2,3,4-tetrahydroisoquinoline-3-carboxylic acid (1.00 g, 3.41 mmol) and triethylamine (1.57 mL, 11.2 mmol) in dry THF (100 mL). The reaction mixture was stirred under N$_2$ at room temperature for 2 h. The mixture was diluted with Et$_2$O (100 mL), washed with saturated NaHCO$_3$, followed by water, and the organic layer was then collected, dried (Na$_2$SO$_4$) and the solvent removed under reduced pressure. The product was then purified by flash chromatography (50% (80% CHCl$_3$:18% CH$_3$OH:2%

NH₄OH) in CHCl₃) to afford (1.52 g, 83%) of 24 as a white foam. ¹HNMR (CDCl₃) δ7.14 (t, 1H, J=8.0 Hz), 6.90 (d, 1H, J=7.0 Hz), 6.75 (m, 2H), 6.63 (m, 3H), 5.74 (br., 1H), 4.81 (br., 1H), 4.57 (br., 1H), 4.39 (m, 1H), 3.92 (br., 1H), 3.27 (d, 1H, J=14.9 Hz), 2.94 (dd, 1H, J=6.2, 15.5 Hz), 2.47–2.16 (m, 5H), 1.97 (m, 2H), 1.76 (m, 2H), 1.51 (s, 9H), 1.40 (m, 1H), 1.21 (s, 3H), 0.85 (d, 3H, J=6.2 Hz), 0.80 (d, 3H, J=6.8 Hz), 0.79 (m, 3H).

(3R)-7-Hydroxy-N-((1S)-1-1[(3R,4R)-4-(3-hydroxyphenyl)-3,4-dimethyl-1-piperidinyllmethyl)2-methylpropyl)-1,2,3,4-tetrahydro-3-isoquinolinecarboxamide (14). Trifluoroacetic acid (16.4 mL, 212 mmol) was added dropwise over 10 min. to a solution of 24 (1.00 g, 1.77 mmol) dry CH₂Cl₂ (50 mL) at −20° C. The reaction was warmed to room temperature and the solvent was removed under reduced pressure. The product was purified by flash chromatography (50% (80% CHCl₃:18% CH₃OH:2% NH40H) in CHCl₃) to afford 14 (0.801 g, 97%) as a white foam. ¹H-NMR (CD₃OD) δ7.11 dt, 1H, J=7.9 Hz), 6.92 (d, 1H, J=8.3 Hz), 6.74 (m, 2H), 6.59 (m, 2H), 6.50 (m, 1H), 4.03 (m, 1H), 3.94 (d, 2H, J=5.9 Hz), 3.54 (dd, 1H, J=4.8, 10.2 Hz), 2.94 (dd, 1H, J=4.7, 15.7 Hz), 2.80 (m, 2H), 2.67–2.37 (m, 5H), 2.27 (dt, 1H, J 4.2, 12.6 Hz), 1.99–1.85 (m, 2H), 1.57 (d, 1H, J=12.7 Hz), 1.30 (s, 3H), 0.95 (m, 6H), 0.74 (d, 3H, J 6.7 Hz).

(3S)-7-Hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (15). Boc-L-7-hydroxy-1,2,3,4-tetrahydroisoquinoline-3-carboxylic acid (107 mg, 1.364 mmol) was added to a solution of 3-[1-(2S-Amino-3-methylbutyl)-3R,4R-dimethyl-4-piperidinyl]phenol (23, 100 mg, 0.364 mmol) in 10 mL of dry THF followed by BOP reagent (177 mg, 0.4 mmol) and TEA (0.166 mL, 1.194 mmol). The reaction mixture was stirred for two hours at room temperature and then 15 mL of ether was added and the mixture was washed with saturated NaHCO₃ and then water. The organic layer was collected, dried over magnesium sulfate and the solvent removed under reduced pressure. The crude product (220 mg) was purified using silica gel column chromatography (gradient: neat CHCl₃ to 50% (CHCl₃:MeOH:NH₄OH, 80:18:2) in CHCl₃). This material was dissolved in five mL of dry CH₂Cl₂ and cooled to −20° C., whereupon TFA (2.7 mL, 0.035 moles) was added drop-wise. The reaction flask was left in a MeOH/ice bath for 10 minutes and then was allowed to warm to room temperature. The solvent was removed under reduced pressure and the residue diluted with CH₂Cl₂ and to this was added saturated NaHCO₃. The organic layer was separated and the solvent was removed under reduced pressure yielding 120 mg of pure (3S)-7-hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide(15). ¹H-NMR (MeOH): 7.09 (t, J=7.8 Hz, 1H), 6.87 (d, J=4.1 Hz, 1H), 6.77 (s, 1H), 6.74 (d, J=0.8 Hz, 1H), 6.58 (dd, J=8.3, 2.3 Hz, 2H), 6.48 (d, J=2.3 Hz, 1h), 4.01–3.95 (m, 1H), 3.90 (s, 2H), 3.51–3.48 (m, 1H), 3.35 (s, 3H), 2.94–2.21 (m, 9H), 1.96 (d, J=13 Hz, 1H), 1.28 (s, 3H), 0.89 (t, 7.2 Hz, 6H), 0.74 (d, J=6.9 Hz, 3H). LRMS (ES) m/z 466.2 (M+H)⁺.

(3R)-N-((1S)-1-{[(3R,4R)-4-(3-Hydroxyphenyl)-3,4-dimethyl-1-piperidinyl]methyl}-2-methylpropyl)-1,2,3,4-tetrahydro-3-isoquinolinecarboxamide (16). 3-[1-(2S-Amino-3-methylbutyl)-3R,4R-dimethyl-4-piperidinyl]phenol (23) was coupled to 1,2,3,4-tetrahydroisoquinoline-3-carboxylic acid as described for compound 15 and de-protected with TFA as previously described to give crude product which was purified by silica preparative thin layer chromatography (50% (CHCl₃:MeOH:NH₄OH, 80:18:2) in CHCl₃, yielding 0.028 g (3R)-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (16). ¹H NMR (CDCl₃): 7.22 (d, J=8.8 Hz, 1H), 7.05–7.13 (m, 3H), 6.98–7.01 (m, 1H), 6.79 (s, 1H), 6.73 (d, J=7.8 Hz, 1H), 6.65 (dd, J=7.9, 1.8 Hz, 1H), 4.05–4.14 (m, 1H), 3.99 (s, 2H), 3.56 (dd, J=10.7, 4.9 Hz, 1H), 3.18 (dd, J=16.5,4.8 Hz, 1H), 2.67–2.82 (m, 3H), 2.31–2.54 (m, 4H), 2.18–2.25 (m, 1H), 1.86–1.96 (m, 2H), 1.52 (d, J=12.9 Hz, 1H), 1.25 (s, 3H), 0.92 (t, J=7.6 Hz, 6H), 0.67 (d, J=6.9 Hz, 3H). LRMS (ES) m/z 450.3.2 (M+H)⁺.

(3R)-2-(N,N-Dimethylglycyl)-7-hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (17). (3R)-7-Hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (14, 0.100 g, 0.285 mmol) was coupled to N,N-dimethylglycine as described above to yield crude product which was purified by flash chromatography (50% (CHCl₃:MeOH:NH₄OH, 80:18:2) in CHCl₃) to afford (3R)-2-(N,N-dimethylglycyl)-7-hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (17, 0.101 g, 86%) as a white foam. LRMS (ES) m/z 551.4 (M+H)⁺.

(3S)-7-Hydroxy-N-((1S)-1-{[(3R,4R)-4-(3-hydroxyphenyl)-3,4-dimethyl-1-piperidinyl]methyl}-2-methylpropyl)-2-methyl-1,2,3,4-tetrahydro-3-isoquinolinecarboxamide(18). Formalin (0.02 mL, 0.215 mmol) was added to a stirring solution of (3R)-7-hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide (14, 100 mg, 0.215 mmol) dissolved in five mL of dry DCE. To this mixture was added Na(OAc)₃ BH (205 mg, 0.97 mmol). The reaction mixture stirred at room temperature for 1.5 hours and then quenched by the addition of sat'd NaHCO₃, until bubbling subsided. This was then extracted three times with a solution of 3:1 CH₂Cl₂:THF and the residue purified using silica gel preparative thin layer chromatography in 60% (CHCl₃:MeOH:NH₄OH, 80:18:2) in CHCl₃ to give pure (3S)-7-Hydroxy-N-((1S)-1-{[(3R,4R)-4-(3-hydroxyphenyl)-3,4-dimethyl-1-piperidinyl]methyl}-2-methylpropyl)-2-methyl-1,2,3,4-tetrahydro-3-isoquinolinecarboxamide(18). ¹H-NMR (MeOH): 7.09 (t, J=3.8 Hz, 1H), 6.9 (d, J=4.5 Hz, 1H), 6.76 (s, 1H), 6.73 (d, J=1.5 Hz, 1H), 6.57 (dd, J=9, 5.3 Hz, 2H), 6.51 (s, 1H), 3.98–3.83 (m, 3H), 3.80 (s, 2H), 3.47 (d, J=16 Hz, 1H), 3.31 (s, 1H), 3.13–2.44 (m, 1H), 2.37 (t, J=18 Hz, 1H), 1.27 (s, 3H), 0.90 (t, J=3 Hz, 6H), 0.71 (d, J=3 Hz, 3H). LRMS (ES) m/z 480.3 (M+H)⁺.

(3R)-3-{[((1S)-1-{[(3R,4R)-4-(3-Hydroxyphenyl)-3,4-dimethyl-1-piperidinyl]methyl}-2-methylpropyl)amino]methyl}-1,2,3,4-tetrahydro-7-isoquinolinol (19). A solution of 2M BH₃.SMe₂ in THF (0.495 mL 0.99 mmol) was added drop-wise to a −20° C.-solution of 14 (46 mg, 0.099 mmol) in 5 mL of dry THF. The reaction refluxed overnight. It was again cooled to −20° C. and 0.647 mL of MeOH was added. Contents stirred at room temperature for one hour. At room temperature, 1M HCl in ether (0.142 mL, 0.142 mmol) was added, and stirred for 30 minutes. The solvent was then removed under reduced pressure. The oil was then dissolved in 3:1 CH₂Cl₂:THF. Then, enough sat'd NaHCO₃ was added to increase the pH to 10. The organic layer was separated and set aside. The aqueous layer was extracted five times with 3:1 $CH_2Cl_2$:THF. The organic layer was dried over sodium sulfate, and the solvent was removed under reduced pressure, yielding a yellowish foam. The crude product (0.03 g) was purified by silica preparative thin layer chromatography using a solvent gradient, starting with 25% ($CHCl_3$:MeOH:$NH_4OH$, 80:18:2) in $CHCl_3$ then 40%, and finally 65%. This afforded 0.006 g of (3R)-3-{[((1S)-1-{[(3R,4R)-4-(3-hydroxyphenyl)-3,4-dimethyl-1-piperidinyl] methyl}-2-methylpropyl)amino]methyl}-1,2,3,4-tetrahydro-7-isoquinolinol (19). $^1$H-NMR (MeOH): 7.12(t, J=5.1 Hz, 1H), 6.90 (d, J=4.1 Hz, 1H), 6.8(d, J=3.9 Hz, 1H), 6.76 (d, J=1.1 Hz, 1h), 6.61 (dd, J=5.8,2.2 Hz, 2H), 6.48 (d, J=1.2 Hz, 1H), 2.88–2.43 (m, 16H), 2.4–1.8 (m, 2H), 1.67 (d, J=13 Hz, 1H), 1.34 (s, 3H), 1.01 (d, J=6.9 Hz, 3H), 0.95 (d, J=6.9 Hz, 3H), 0.81 (d, J=3.4 Hz, 3H). LRMS (ES) m/z 452.3 (M+H)$^+$.

(3R)-3-{[((1S)-1-{[(3R,4R)-4-(3-Hydroxyphenyl)-3,4-dimethyl-1-piperidinyl]methyl}-2-methylpropyl)amino] methyl}-2-methyl-1,2,3,4-tetrahydro-7-isoquinolinol(20). Tert-Butyl-(3R)-3-{[((1S)-1-{[(3R,4R)-4-(3-hydroxyphenyl)-3,4-dimethyl-1-piperidinyl]methyl}-2-methylpropyl)amino]carbonyl}-3,4-dihydrohydro-2(1H)-isoquinolinecarboxylate (24) (57 mg, 0.119 mmol) was dissolved in 10 mL of dry THF and added drop-wise to a slurry of lithium aluminum hydride (30 mg) in THF cooled to (−) 20° C. The reaction was heated at reflux overnight and then, 1 mL of 1N NaOH was added at (−) 20° C., until a flocculent white precipitate was observed and bubbling ceased. This was filtered and the cake washed with ethyl ether. The combined organic layers were washed with water and dried over $MgSO_4$. After removal of the solvent, the crude material (40 mg) was purified using silica gel preparative thin layer chromatography using 40% ($CHCl_3$:MeOH:$NH_4OH$, 80:18:2) in $CHCl_3$. LRMS (ES) m/z 480.3 (M+H)$^+$.

3-[1-(2S-Amino-3-methylbutyl)-3S,4S-dimethyl-4-piperidinyl]phenol (26). (+)-(3S,4S)-Dimethyl-4-(3-hydroxyphenyl)piperidine (25) (0.500 g, 2.44 mmol), BOC-L-valine (0.5292 g, 2.44 mmol), BOP reagent (1.109 g, 2.44 mmol) and TEA (0.74 mL, 5.36 mmol) were combined with THF (31 mL) and stirred 1 hr at room temperature. The mixture was poured into ether (100 mL) and water (31 mL) and shaken. The organic layer was washed once with saturated $NaHCO_3$ (30 mL) and once with brine (30 mL). Hexane was added to the organic layer until it turned cloudy. After drying with anhydrous sodium sulfate, the solvent was removed under reduced pressure. This was dissolved in dichloromethane (9 mL) and cooled to −20 ° C. Trifluoroacetic acid (6 mL) was added dropwise over 2 min. The reaction was stirred 30 min. at −20° C., followed by 30 min stirring after the cold bath was removed. The mixture was poured onto saturated $NaHCO_3$ (83 mL) and chloroform (31 mL). The solution was adjusted to pH 10 with solid $NaHCO_3$. The mixture was rinsed into a separatory funnel with a small amount of MeOH and the aqueous layer was extracted 5 times with 3:1 $CH_2Cl_2$/THF. The organic layers were dried with anhydrous sodium sulfate and the solvent was removed under reduced pressure. This was dissolved in THF (31 mL) and cooled to −20° C. Borane-methyl sulfide complex (11.65 mL, 0.0233 mol) was added dropwise and the mixture was refluxed 3 hr. The reaction was cooled to −20° C., whereupon methanol (15 mL) was added dropwise and the mixture was stirred for 1 hr at room temperature. 1 M HCl (3.42 mL) was added and the reaction was stirred 30 min. at room temperature. The solvent was removed under reduced pressure, then 3:1 $CH_2Cl_2$/THF (20 mL) and water (20 mL) were added. Saturated $NaHCO_3$ was added to pH 9. The organic layer was then removed and the water layer was saturated with NaCl. The aqueous layer was extracted 3 times with 3:1 $CH_2Cl_2$/THF. The organic layers were combined and dried with anhydrous sodium sulfate and the solvent was removed under reduced pressure. The yellow-white foam was purified via silica gel chromatography using a gradient of 0–10% MeOH in $CHCl_3$ to afford 3-[1-(2S-Amino-3-methylbutyl)-3S,4S-dimethyl-4-piperidinyl] phenol (26) (0.5420 g. 1.87 mmol, 76.6%) as a yellow-white foam. $^1$H NMR ($CDCl_3$): 7.13 (t, J=7.9 Hz, 1H), 6.76 (d, J=7.9 Hz, 1H), 6.69 (s, 1H), 6.64 (dd, J=7.9 Hz, 1H), 4.25 (br s, 3H), 2.89 (d, J=5.1 Hz, 1H), 2.79 (dd, J=11.2, 2.5 Hz, 1H), 2.72–2.75 (m, 1H), 2.42 (d, J=11.2 Hz, 1H), 2.36 (dd, J=12.4, 2.9 Hz, 1H), 2.22 (d, J=8.4 Hz, 2H), 1.98 (d, J=6.5 Hz, 1H), 1.61–1.72 (m, 1H), 1.56 (d, J=9.7 Hz, 1H), 1.28 (s, 3H), 0.96 (d, 6.9 Hz, 3H), 0.93 (d, J=6.9 Hz, 3H), 0.79 (d, J=6.9 Hz, 3H).

Tert-Butyl-(3R)-7-hydroxy-3-{[((1S)-1-{[(3S,4S)-4-(3-hydroxyphenyl)-3,4-dimethyl-1-piperidinyl]methyl}-2-methylpropyl)amino]carbonyl}-3,4-dihydrohydro-2(1H)-isoquinolinecarboxylate (27). 3-[1-(2S-Amino-3-methylbutyl)-3S,4S-dimethyl-4-piperidinyl]phenol (26) (0.200 g, 0.69 mmol), Boc-D-7-hydroxy-1,2,3,4-tetrahydroisoquinoline-3-carboxylic acid (0.2119 g, 0.72 mmol), TEA (0.331 mL, 2.37 mmol), and BOP reagent (0.351 g, 0.80 mmol) were combined in THF (21 mL) and stirred at room temperature 2 hr. Ether (21 mL) was added and washed once with saturated $NaHCO_3$ and once with water. The organic layers were combined and dried with anhydrous sodium sulfate and the solvent was removed under reduced pressure. The crude product was purified by silica gel chromatography. 25% ($CHCl_3$:MeOH:$NH_4OH$, 80:18:2) in $CHCl_3$ was used until the cloudy band was collected, then 33% ($CHCl_3$:MeOH:$NH_4OH$, 80:18:2) in $CHCl_3$ was used to collect tert-butyl-(3S)-7-hydroxy-3-{ [((1S)-1-{[(3S,4S)-4-(3-hydroxyphenyl)-3,4-dimethyl-1-piperidinyl]methyl}-2-methylpropyl)amino]carbonyl}-3,4-dihydrohydro-2(1H)-isoquinolinecarboxylate (27) (0.2768 g, 0.49 mmol, 71.1%). $^1$H NMR ($CDCl_3$): 7.19 (t, J=7.8 Hz, 1H), 6.94 (d, J=8.2 Hz, 1H), 6.71–6.82 (m, 5H), 6.46–6.51 (m, 1H), 6.19 (br s, 1H), 4.99 (br s, 1H), 4.81 (br s, 1H), 4.47 (dd, J=28.7, 16.3 Hz, 2H), 3.79 (br s, 1H), 3.40–3.49 (m, 1H), 2.83–2.87 (m, 1H), 2.50 (br s, 1H), 2.28–2.34 (m, 2H), 2.18 (br s, 2H), 2.03–2.04 (m, 1H), 1.86–1.88 (m, 2H), 1.49 (s, 9H), 1.18 (br s, 3H), 0.85 (d, J=6.9 Hz, 3H), 0.84 (d, J=6.9 Hz, 3H), 0.75 (d, J=6.9 Hz, 3H).

(3R)-7-Hydroxy-N-((1S)-1-{[(3S,4S)-4-(3-hydroxyphenyl)-3,4-dimethyl-1-piperidinyl]methyl}-2-methylpropyl)-1,2,3,4-tetrahydro-3-isoquinolinecarboxamide (21). (3R)-7-Hydroxy-N-((1S)-1-{[(3S,4S)-4-(3-hydroxyphenyl)-3,4-dimethyl-1-piperidinyl] methyl}-2-methylpropyl)-1,2,3,4-tetrahydro-3-isoquinolinecarboxamide (21). Tert-Butyl-(3S)-7-hydroxy-3-{[((1S)-1-{[(3S,4S)-4-(3-hydroxyphenyl)-3,4-dimethyl-1-piperidinyl]methyl}-2-methylpropyl)amino]carbonyl}-3,4-dihydrohydro-2(1H)-isoquinolinecarboxylate (27) (0.2088 g, 0.37 mmol) was dissolved in dichloromethane (11 mL) and cooled to −20° C. TFA (3.50 mL) was added dropwise over 10 min. The reaction was stirred for 10 min. at −20° C., then stirred 30 min. after removing the cold bath. The solvent was removed under reduced pressure, and the remaining oil was allowed to sit under nitrogen atmosphere for 5 min. Dichloromethane (11 mL) and saturated $NaHCO_3$ (11 mL) were added and the aqueous layer was extracted twice with dichloromethane after shaking. The combined organic layers were later discarded, as they contained no desired product. The aqueous layer was then extracted 3 times with 3:1 CH$_2$Cl$_2$/THF. The organic layers were dried with anhydrous sodium sulfate and the solvent was removed under reduced pressure to yield pure (3R)-7-hydroxy-N-((1S)-1-{[(3S,4S)-4-(3-hydroxyphenyl)-3,4-dimethyl-1-piperidinyl]methyl}-2-methylpropyl)-1,2,3,4-tetrahydro-3-isoquinolinecarboxamide (21) (0.120 g, 0.26 mmol, 69.8%). $^1$H NMR (MeOH): 7.09 (t, J=7.9 Hz, 1H), 6.92 (d, J=8.3 Hz, 1H), 6.77 (s, 1H), 6.73 (d, J=2.3 Hz, 1H), 6.56–6.61 (m, 2H), 6.49 (d, J=2.3 Hz, 1H), 3.96–4.03 (m, 1H), 3.92 (d, J=6.5 Hz, 2H), 3.56 (dd, J=10.0, 4.9 Hz, 1H), 2.93 (dd, J=15.7, 4.9 Hz, 1H), 2.83 (d, J=9.9 Hz, 2H), 2.52–2.66 (m, 2H), 2.18–2.48 (m, 5H), 1.86–1.97 (m, 2H), 1.53 (d, J=12.5 Hz, 1H), 1.27 (s, 3H), 0.92 (t, J=6.6 Hz, 6H), 0.76 (d, J=7.0 Hz, 3H). LRMS (ES) m/z 466.2 (M+H)$^+$.

REFERENCES (1) Aldrich, J. V. Analgesics. In *Burger's Medicinal Chemistry and Drug Discovery*, Wolff, M. E. Eds.; John Wiley & Sons: New York, 1996; Vol. 3.

(2) Volpicelli, J. R.; Alterman, A. I.; Hayashida, M.; O'Brien, C. P. Naltrexone in the treatment of alcohol dependence. *Arch. Gen. Psychiatry* 1992, 49, 876–879.

(3) Volpicelli, J. R.; Watson, N. T.; King, A. C.; Sherman, C. E.; O'Brien, C. P. Effect of naltrexone on alcohol "high" in alcoholics. *Am. J. Psychiatry* 1995, 152, 613–615.

(4) Marki, A.; Monory, K.; Otvos, F.; Toth, G.; Krassnig, R.; Schmidhammer, H.; Traynor, J. R.; Roques, B. P.; Maldonado, R.; Borsodi, A. Mu-opioid receptor specific antagonist cyprodime: characterization by in vitro radioligand and [35S]GTPgammaS binding assays. *Eur J Pharmacol* 1999, 383(2), 209–14.

(5) Portoghese, P. S. The design of δ-selective opioid receptor antagonists. *II Fannaco* 1993, 48(2), 243–251.

(6) Portoghese, P. S.; Lipkowski, A. W.; Takemori, A. E. Binaltorphimine and nor-binaltorphimine, potent and selective κ-opioid receptor antagonists. *Life Sci.* 1987, 40(13), 1287–1292.

(7) Olmsted, S. L.; Takemori, A. E.; Portoghese, P. S. A remarkable change of opioid receptor selectivity on the attachment of a peptidomimetic κ address element to the δ antagonist, natrindole: 5'-[N$^2$-alkylamidino)methyl] naltrindole derivatives as a novel class of κ opioid receptor antagonists. *J. Med. Chem.* 1993, 36(1), 179–180.

(8) Jones, R. M.; Hjorth, S. A.; Schwartz, T. W.; Portoghese, P. S. Mutational evidence for a common kappa antagonist binding pocket in the wild-type kappa and mutant mu[K303E] opioid receptors. *J Med Chem* 1998, 41(25), 4911–4.

(9) Schwyzer, R. ACTH: A short introductory review. *Ann. N. Y Acad. Sci.* 1977, 247, 3–26.

(10) Trujillo, K. A.; Akil, H. Changes in prodynorphin peptide content following treatment with morphine or amphetamine: possible role in mechanisms of action of drug of abuse. *NIDA Res Monogr* 1989, 95, 550–1.

(11) Smiley, P. L.; Johnson, M.; Bush, L.; Gibb, J. W.; Hanson, G. R. Effects of cocaine on extrapyramidal and limbic dynorphin systems. *J Pharmacol Exp Ther* 1990, 253(3), 938–43.

(12) Corbett, A. D.; Paterson, S. J.; McKnight, A. T.; Magnan, J.; Kosterlitz, H. W. Dynorphin and dynorphin are ligands for the kappa-subtype of opiate receptor. *Nature* 1982, 299(5878), 79–81.

(13) Spanagel, R.; Herz, A.; Shippinberg, T. A. Opposing tonically active endogenous opioid systems modulate the mesolimbic dopaniinergic pathway. *Proc. Natl. Acad. Sci. U.S.A.* 1992, 89, 2046–2050.

(14) Spanagel, R.; Shippenberg, T. S. Modulation of morphine-induced sensitization by endogenous κ opioid systems in the rat. *Neurosci. Lett.* 1993, 153, 232–236.

(15) Zadina, J. E.; Hackler, L.; Ge, L.-J.; Kastin, A. J. A potent and selective endogenous agonist for the μ-opiate receptor. *Nature* 1997, 386, 499–502.

(16) Zinunerman, D. M.; Nickander, R.; Homg, J. S.; Wong, D. T. New structural concepts for narcotic antagonists defined in a 4-phenylpiperidine series. *Nature* 1978, 275, 332–334.

(17) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence*, 1978, pp. 237–247.

(18) Zimmerman, D. M.; Smits, S. E.; Hynes, M. D.; Cantrell, B. E.; Reamer, M.; Nickander Structural requirements for affinity and intrinsic activity at the opiate receptor defined in 4-phenylpiperidine and related series. In *Problems of Drug Dependence 1981, Proceedings of the 43rd Annual Scientific Meeting of the Committee on Problems of Drug Dependence, Inc.*, Harris, L. S. Eds.; 1981, pp. 112–116.

(19) Zimmerman, D. M.; Smits, S. E.; Hynes, M. D.; Cantrell, B. E.; Reamer, M.; Nickander, R. Structural requirements for affinity and intrinsic activity at the opiate receptor defined in 4-phenylpiperidine and related series. In *Problems of Drug Dependence, 1981, Proceedings of the 43rd Annual Scientific Meeting*, The committee on Problems of Drug Dependence, Inc., Harris, L. S. Eds.; Committee on Problems of Drug Dependence, Inc.: 1982; Vol. NIDA Research Monograph 41, pp. 112–118.

(20) Zimmerman, D. M.; Cantrell, B. E.; Swartzendruber, J. K.; Jones, N. D.; Mendelsohn, L. G.; Leander, J. D.; Nickander, R. C. Synthesis and analgesic properties of N-substituted trans-4a-aryldecahydroisoquinolines. *J. Med. Chem.* 1988, 31, 555–560.

(21) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for μ and κ opioid receptors. *J. Med. Chem.* 1993, 36(20), 2833–2841.

(22) Zimnerman, D. M.; Hermann, R. B.; Mitch, C. H.; Shaw, W. N.; Mendelsohn, L.G.; Leander, J. D. Opioid receptor antagonists: Comparison of trans-3,4-dimethyl-4-phenylpiperidines and their use in the development of a model of opioid receptors. *Pharmacol. Rev.* in press.

(23) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and μ receptor subtype-selectivity in (+)-(3R, 4R)-dimethyl-4-(3-hydroxyphenyl)piperidine opioid antagonists. *J. Med. Chem.* 1998, 41(11), 1980–1990.

(24) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of opioid κ receptor subtype-selective N-substituent for (+)-(3R,4R)-dimethyl-4-(3-hydroxyphenyl)piperidine. *J. Med. Chem.* 1998, 41(26), 5188–5197.

(25) Wemer, J. A.; Cerbone, L. R.; Frank, S. A.; Ward, J. A.; Labib, P.; Tharp-Taylor, R. W.; Ryan, C. W. Synthesis of trans-3,4-dimethyl-4-(3-hydroxyphenyl)piperidine opioid antagonists: Application of the cis-thermal elimination of carbonates to alkaloid synthesis. *J. Org. Chem.* 1996, 61, 587–597.

Obviously, numerous modifications and variations of the present invention are possible in light of the above teachings. It is therefore to be understood that within the scope of the appended claims, the invention may be practiced otherwise than as specifically described herein.

What is claimed is:

1. A kappa opioid receptor antagonist compound represented by the formula (I):

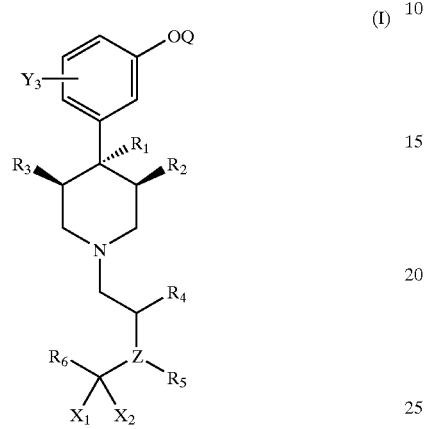
(I)

wherein Q is H or $COC_{1-8}$ alkyl;

$R_1$ is $C_{1-8}$ alkyl, or one of the following structures:

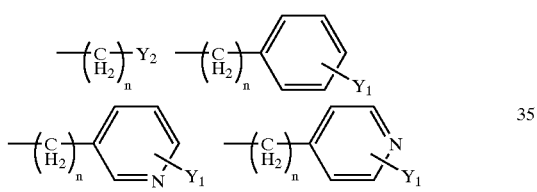

$Y_1$ is H, OH, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH_2(CH_2)_nY_2$;

$Y_2$ is H, $CF_3$, $CO_2R_9$, $C_{1-6}$alkyl, $NR_{10}R_{11}$, $NHCOR_{12}$, $NHCO_2R_{12}$, $CONR_3R_{14}$, $CH_2OH$, $CH_2OR_8$, or $COCH_2R_9$;

$Y_3$ is H, OH, Br, Cl, F, CN, $CF_3$, $NO_2$, $N_3$, $OR_8$, $CO_2R_9$, $C_{1-6}$ alkyl, $NR_{10}R_{11}$, $NHCOR_{12}$, $NHCO_2R_{12}$, $CONR_{13}R_{14}$, or $CH2(CH_2)_nY_2$;

$R_2$ is H, $C_{1-8}$ alkyl, $C_{3-8}$alkenyl, $C_{3-8}$ alkynyl or $CH_2$aryl substituted by one or more groups $Y_1$;

$R_3$ is H, $C_{1-8}$ alkyl, $C_{3-8}$ alkenyl, $C_{3-8}$ alkynyl or $CH_2$aryl substituted by one or more groups $Y_1$;

wherein $R_2$ and $R_3$ may be bonded together to form a $C_{2-8}$ alkyl group;

$R_4$ is hydrogen, $C_{1-8}$ alkyl, $CO_2C_{1-8}$ alkylaryl substituted by one or more groups $Y_1$, $CH_2$aryl substituted by one or more groups $Y_1$ or $CO_2C_{1-8}$ alkyl;

Z is N, O or S; when Z is O or S there is no $R_5$ $R_5$ is H, $C_{1-8}$ alkyl, $C_{3-8}$ alkenyl, $C_{3-8}$ alkynyl, $CH_2CO_2C_{1-8}$ alkyl, $CO_2C_{1-8}$ alkyl or $CH_2$aryl substituted by one or more groups $Y_1$;

n is 0, 1, 2 or 3;

$R_6$ is a group selected from the group consisting of structures (a)–(w) and (cc)–(bbb):

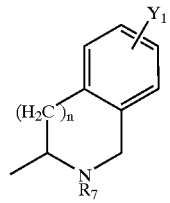
(a)

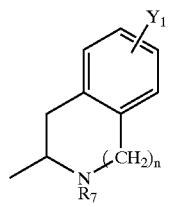
(b)

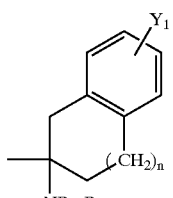
(c)

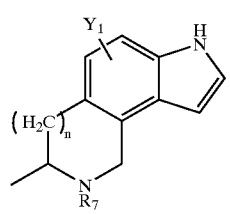
(d)

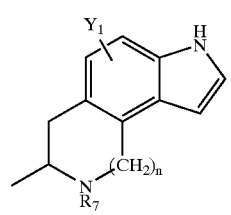
(e)

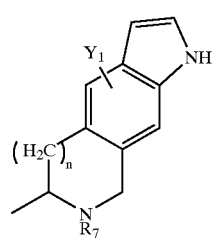
(f)

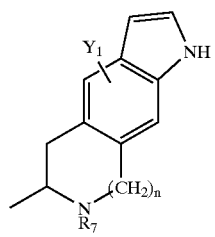
(g)

-continued
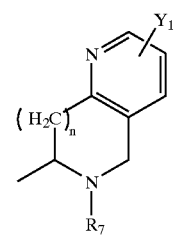 (h)
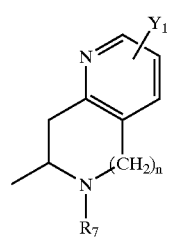 (i)
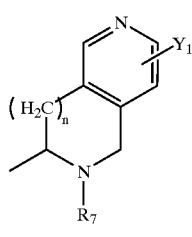 (j)
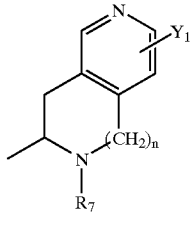 (k)
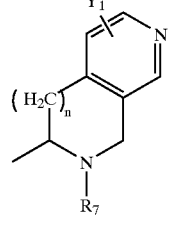 (l)
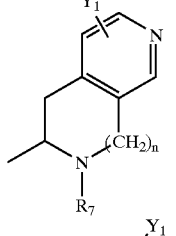 (m)
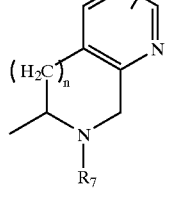 (n)
-continued
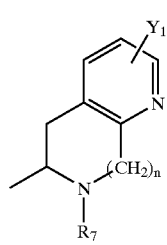 (o)
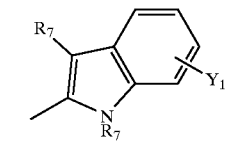 (p)
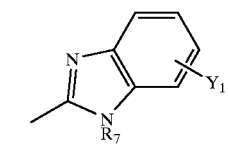 (q)
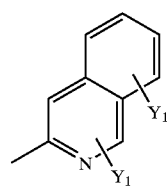 (r)
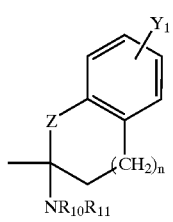 (s)
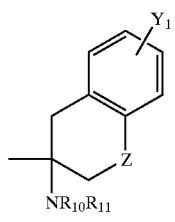 (t)
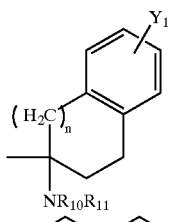 (u)
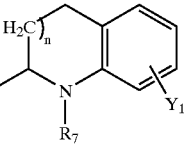 (v)

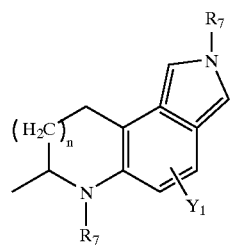 (w)
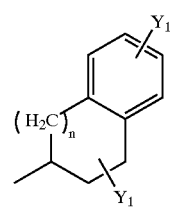 (cc)
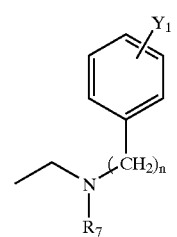 (dd)
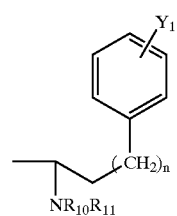 (ee)
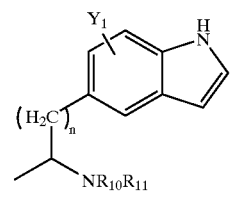 (ff)
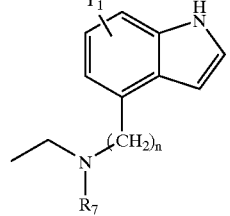 (gg)
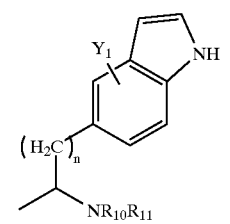 (hh)
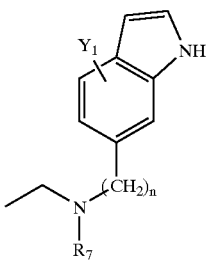 (ii)
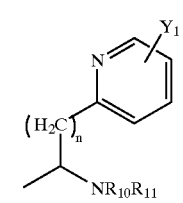 (jj)
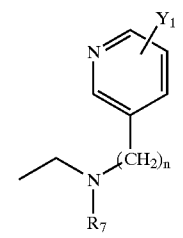 (kk)
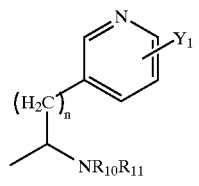 (ll)
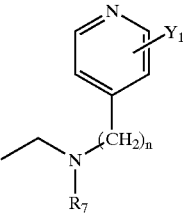 (mm)
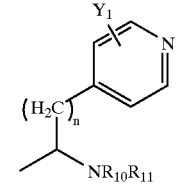 (nn)
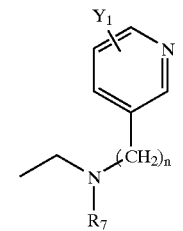 (oo)

-continued (pp)

(qq)

(rr)

(ss)

(tt)

(uu)

(vv)

(ww)

-continued (xx)

(yy)

(zz)

(aaa)

(bbb)

$X_1$ is hydrogen, $C_{1-8}$ alkyl, $C_{3-8}$alkenyl, or $C_{3-8}$alkynyl;
$X_2$ is hydrogen, $C_{1-8}$alkyl, $C_{3-8}$alkenyl, or $C_{3-8}$alkynyl;
or $X_1$ and $X_2$ together form =O, =S, or =NH;

$R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, $CH_2(CH_2)_nY_2$, or $C(=NH)NR_{16}R_{17}$;

$R_8$ is H, $C_{1-8}$alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_9$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{10}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{11}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{12}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{13}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{14}$ is H, $C_{1-8}$ alkyl, $CH_2$ aryl substituted by one or more substitiients H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{15}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{16}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl; and $R_{17}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl and pharmaceutically acceptable salts thereof.

2. The kappa opioid receptor antagonist compound of claim 1, wherein $R_1$, $R_4$, $R_5$, $Y_1$, $Y_2$, Z, n, $X_1$, $X_2$, and $R_7$–$R_{17}$ are as in claim 1;

$Y_3$ is H;

$R_2$ and $R_3$ are each, independently, H, $C_{1-8}$ alkyl, $C_{3-8}$ alkynyl, $C_{3-8}$ alkynyl, or $CH_2$aryl substituted by one or more substituents $Y_1$; and $R_6$ is a group having a formula selected from the group consisting of structures (a)–(w) and (cc).

3. The kappa opioid receptor antagonist compound of claim 1, wherein $Y_1$, $Y_2$, $R_4$, $R_5$, Z, n, $X_1$, $X_2$ and $R_8R_{15}$ are as in claim 1;

$R_1$ is $C_{1-8}$ alkyl, or one of the following structures:

$-\left(\begin{smallmatrix}C\\H_2\end{smallmatrix}\right)_n Y_2$   $-\left(\begin{smallmatrix}C\\H_2\end{smallmatrix}\right)_n \!\!\!\!\!\!\diagup\!\!\!\!\!\diagdown\!\!\!\!\!\!-Y_1$ $R_2$ and $R_3$ are each, independently, H or $C_{1-8}$ alkyl, wherein $R_2$ and $R_3$ cannot both be H at the same time;

$R_6$ is a formula selected from the structures (a)–(r); and $R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

4. The kappa opioid receptor antagonist compound of claim 1, wherein $Y_1$, Z, n, $X_1$, $X_2$ and $R_8$–$R_{15}$ are as in claim 1;

$R_1$ is $C_{1-8}$ alkyl;

$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each, independently, H or methyl, wherein $R_2$ and $R_3$ cannot both be H at the same time;

$R_4$ is H, $C_{1-8}$ alkyl, $CO_2C_{1-8}$alkyl, or $CH_2$ aryl substituted by one or more substituents $Y_1$ and the stereocenter adjacent to $R_4$ is in an (S) configuration;

$R_5$ is H, $C_{1-8}$ alkyl, $CH_2CO_2C_{1-8}$ alkyl;

$R_6$ is a group having a formula selected from the group consisting of structures (a)–(c) and (h)–(o); and $R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

5. The kappa opioid receptor antagonist compound of claim 1, wherein $Y_1$, Z, n, $X_1$, $X_2$ and $R_8$–$R_{14}$ are as in claim 1;

$R_1$ is methyl, $Y_2$ is H, $CF_3$, $CO_2R_9$, $C_{1-6}$ alkyl, $NHR_{10}R_{11}$, $NHCOR_{12}$, $NHCO2R_{12}$, $CONR_{13}R_{14}$, $CH_2OH$, $CH_2OR_8$, or $COCH_2R_9$;

$Y_3$ is H;

$R_2$ and $R_3$ are each H or methyl, such that when $R_2$ is H, $R_3$ is methyl and vice versa;

$R_4$ is $C_{1-8}$ alkyl, or $CO_2C_{2-8}$ alkyl, and the stereocenter adjacent to $R_4$ has a configuration of (S);

$R_5$ is H;

$R_6$ is a group having a formula selected from the group consisting of structures (a) and (b); and $R_7$ is H, $C_{1-8}$ alkyl, $CH_2$aryl substituted by one or more substituents $Y_1$ or $CH_2(CH_2)_nY_2$.

6. The kappa opioid receptor antagonist of claim 1, wherein said compound is a compound selected from formulae 14–21 as follows:

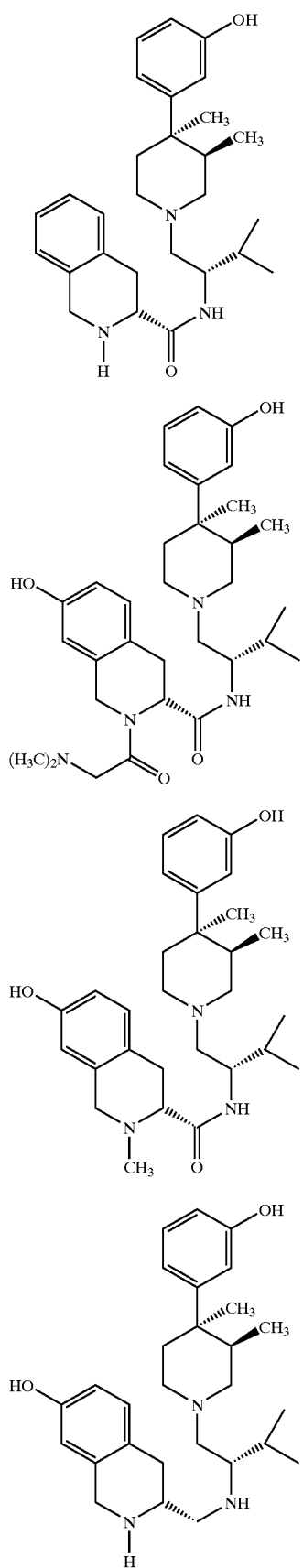
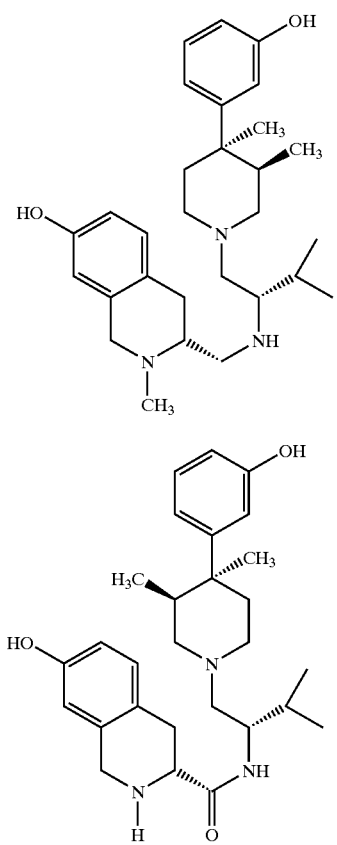
7. A pharmaceutical composition comprising:
an effective amount of a kappa opioid receptor antagonist and a physiologically acceptable carrier, wherein the kappa opioid receptor antagonist is a compound of formula (I):
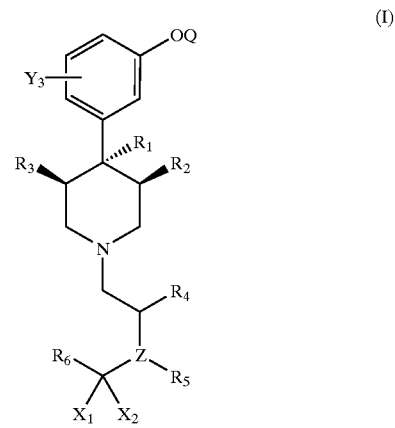
wherein Q is H or $COC_{1-8}$ alkyl;
$R_1$ is $C_{1-8}$ alkyl, or one of the following structures:
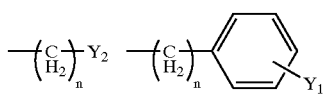

-continued

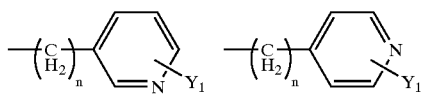

Y₁ is H, OH, Br, Cl, F, CN, CF₃, NO₂, N₃, OR₈, CO₂R, C₁₋₆ alkyl, NR₁₀R₁₁, NHCOR₁₂, NHCO₂R₁₂, CONR₁₃R₁₄, or CH2(CH₂)$_n$Y₂;

Y₂ is H, CF₃, CO₂R₉, C₁₋₆alkyl, NR₁₀R11, NHCOR₁₂, NHCO2R₁₂, CONR₃R₁₄, CH₂OH, CH₂OR₈, or COCH₂R₉;

Y₃ is H, OH, Br, Cl, F, CN, CF₃, NO₂, N₃, OR₈, CO₂R₉, C₁₋₆ alkyl, NR₁₀R₁₁, NHCOR₁₂, NHCO₂R₁₂, CONR₁₃R₁₄, or CH₂(CH₂)$_n$Y2;

R₂ is H, C₁₋₈ alkyl, C₃₋₈ alkenyl, C₃₋₈ alkynyl or CH₂aryl substituted by one or more groups Y₁;

R₃ is H, C₁₋₈ alkyl, C₃₋₈ alkenyl, C₃₋₈ alkynyl or CH₂aryl substituted by one or more groups Y₁;

wherein R₂ and R₃ may be bonded together to form a C₂₋₈ alkyl group;

R₄ is hydrogen, C₁₋₈ alkyl, CO₂C₁₋₈ alkylaryl substituted by one or more groups Y₁, CH₂aryl substituted by one or more groups Y₁, or CO₂C₁₋₈ alkyl;

Z is N, O or S; when Z is O or S, there is no R₅

R₅ is H, C₁₋₈ alkyl, C₃₋₈ alkenyl, C₃₋₈ alkynyl, CH₂CO₂C₁₋₈ alkyl, CO₂C₁₋₈ alkyl or CH₂aryl substituted by one or more groups Y₁;

n is 0, 1, 2 or 3;

R₆ is a group selected from the group consisting of structures (a)–(w) and (cc)–(bbb):

(a)
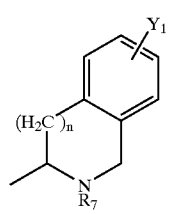

(b)
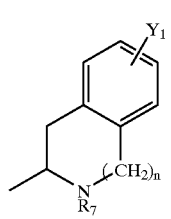

(c)
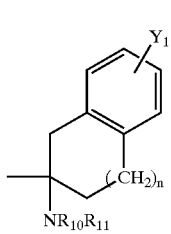

(d)
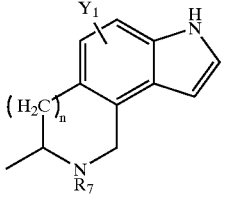

(e)
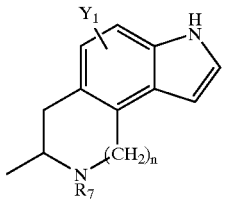

(f)
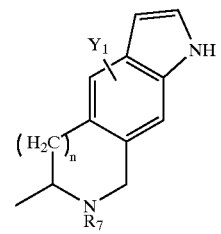

(g)
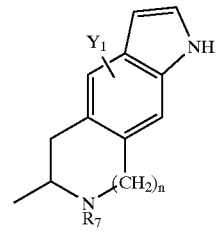

(h)
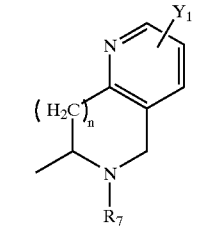

(i)
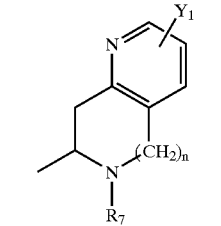

(j)
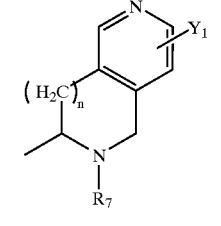

-continued

-continued
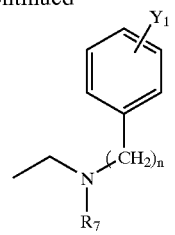 (dd)
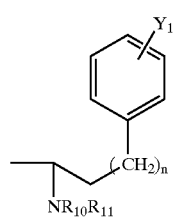 (ee)
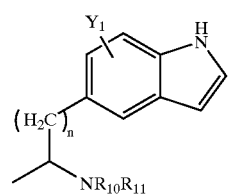 (ff)
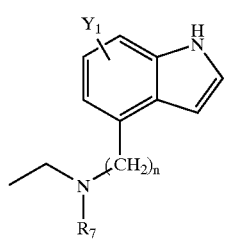 (gg)
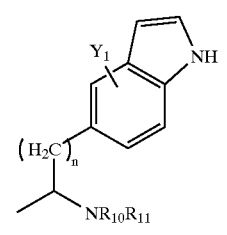 (hh)
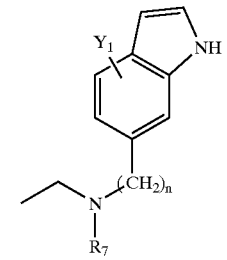 (ii)
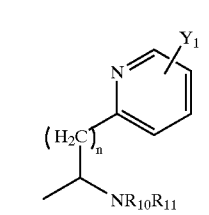 (jj)
-continued
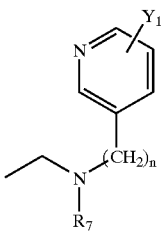 (kk)
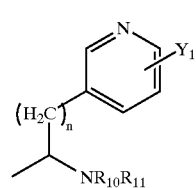 (ll)
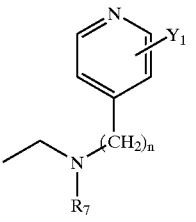 (mm)
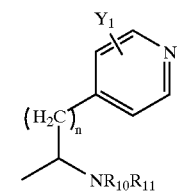 (nn)
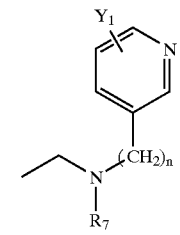 (oo)
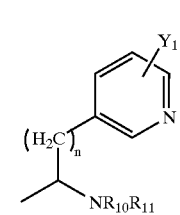 (pp)
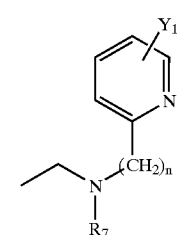 (qq)

(rr) 

(ss) 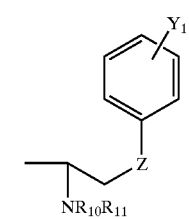

(tt) 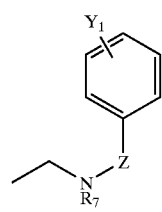

(uu) 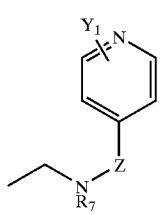

(vv) 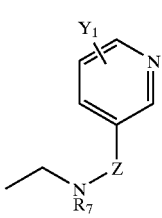

(ww) 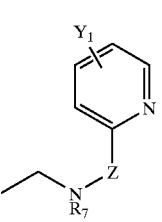

(xx) 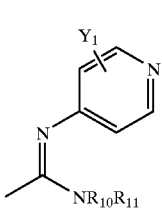

(yy) 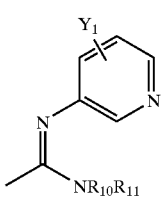

(zz) 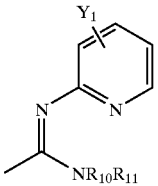

(aaa) 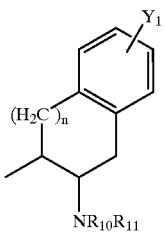

(bbb) 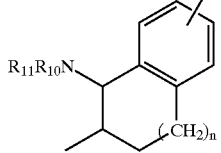

$X_1$ is hydrogen, $C_{1-8}$ alkyl, $C_{3-8}$alkenyl, or $C_{3-8}$alkynyl;

$X_2$ is hydrogen, $C_{1-8}$alkyl, $C_{3-8}$alkenyl, or $C_{3-8}$alkynyl;

or $X_1$ and $X_2$ together form =O, =S, =NH;

$R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, $CH_2(CH_2)_nY_2$, or $C(=NH)NR_{16}R_{17}$;

$R_8$ is H, $C_{1-8}$alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_9$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{10}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{11}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{12}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{13}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{14}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{15}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl;

$R_{16}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl; and $R_{17}$ is H, $C_{1-8}$ alkyl, $CH_2$ aryl substituted by one or more substituents H, OH, Br, Cl, F, CN, $CF_3$, $NO_2$, $N_3$, $C_{1-6}$ alkyl, or $CH_2(CH_2)_nY_2'$; wherein $Y_2'$ is H, $CF_3$, or $C_{1-6}$alkyl or a pharmaceutically acceptable salt thereof.

8. The pharmaceutical composition of claim 7, wherein said kappa opioid receptor antagonist is a compound of formula (I), wherein $R_1$, $R_4$, $R_5$, $Y_1$, $Y_2$, Z, n, $X_1$, $X_2$, and $R_7$–$R_{17}$ are as in claim 7;

$Y_3$ is H;

$R_2$ and $R_3$ are each, independently, H, $C_{1-8}$ alkyl, $C_{3-8}$ alkenyl, $C_{3-8}$ alkynyl, or $CH_2$aryl substituted by one or more substituents $Y_1$; and $R_6$ is a group having a formula selected from the group consisting of structures (a)–(w) and (cc).

9. The pharmaceutical composition of claim 7, wherein said kappa opioid receptor antagonist is a compound of formula (1), wherein $Y_1$, $Y_2$, $R_4$, $R_5$, Z, n, $X_1$, $X_2$ and $R_8$–$R_{15}$ are as in claim 7;

$R_1$ is $C_{1-8}$ alkyl, or one of the following structures:

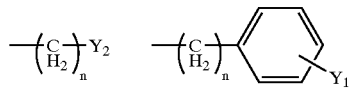

$Y_3$ is H;

$R_2$ and $R_3$ are each, independently, H or $C_{1-8}$ alkyl, wherein $R_2$ and $R_3$ cannot both be H at the same time;

$R_6$ is a formula selected from the structures (a)–(r) shown above; and $R_7$ is H, $C_{1-8}$ alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

10. The pharmaceutical composition of claim 7, wherein said kappa opioid receptor antagonist is a compound of formula (I), wherein $Y_1$, Z, n, $X_1$, $X_2$ and $R_8$–$R_{15}$ are as noted-above in claim 7;

$R_1$ is $C_{1-8}$ alkyl;

$Y_2$ is H, $CF_3$, $CO_2R_9$, $C_{1-6}$ alkyl, $NR_{10}R_{11}$, $NHCOR_{12}$, $NHCO_2R_{12}$, $CONR_{13}R_{14}$, $CH_2OH$, $CH_2OR_8$, or $COCH_2R_9$;

$Y_3$ is H;

$R_2$ and $R_3$ are each, independently, H or methyl, wherein $R_2$ and $R_3$ cannot both be H at the same time;

$R_4$ is H, $C_{1-8}$ alkyl, $CO_2C_{1-8}$alkyl, or $CH_2$ aryl substituted by one or more substituents $Y_1$ and the stereocenter adjacent to $R_4$ is in an (S) configuration;

$R_5$ is H, $C_{1-8}$ alkyl, $CH_2CO_2C_{1-8}$ alkyl;

$R_6$ is a group having a formula selected from the group consisting of structures (a)–(c) and (h)–(o); and $R_7$ is H, $C_{1-8}$alkyl, $CH_2$aryl substituted by one or more substituents $Y_1$, $NR_{10}R_{11}$, $NHCOR_{12}$, $NHCO_2R_{13}$, $CONR_{14}R_{15}$, or $CH_2(CH_2)_nY_2$.

11. The pharmaceutical composition of claim 7, wherein said kappa opioid receptor antagonist is a compound of formula (1), wherein $Y_1$, Z, n, $X_1$, $X_2$ and $R_8$–$R_{14}$ are as in claim 7;

$R_1$ is methyl, $Y_2$ is H, $CF_3$, $CO_2R_9$, $C_{1-6}$ alkyl, $NR_{10}R_{11}$, $NHCOR_{12}$, $NHCO_2R12$, $CONR_{13}R_{14}$, $CH2OH$, $CH_2OR_8$, or $COCH_2R_9$;

$Y_3$ is H;

$R_2$ and $R_3$ are each H or methyl, such that when $R_2$ is H, $R_3$ is methyl and vice versa;

$R_4$ is $C_{1-8}$ alkyl, or $CO_2C_{1-8}$ alkyl, and the stereocenter adjacent to $R_4$ has a configuration of (S);

$R_5$ is H;

$R_6$ is a group having a formula selected from the group consisting of structures (a) and (b); and $R_7$ is H, $C_{1-8}$ alkyl, $CH_2$aryl substituted by one or more substituents Y, or $CH_2(CH_2)_nY_2$.

12. The pharmaceutical composition of claim 7, wherein said kappa opioid receptor antagonist is a compound selected from formulae 14–21 as follows:

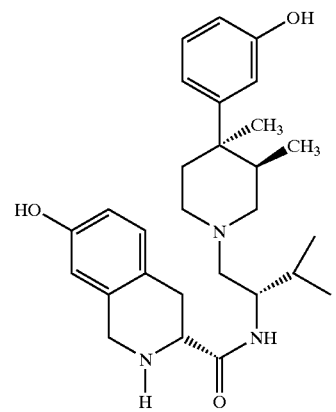

14

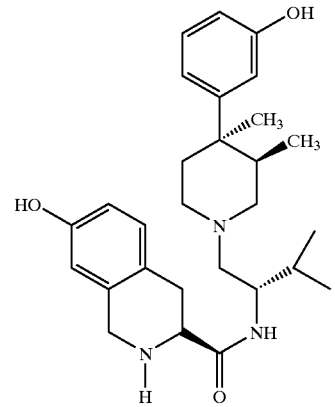

15

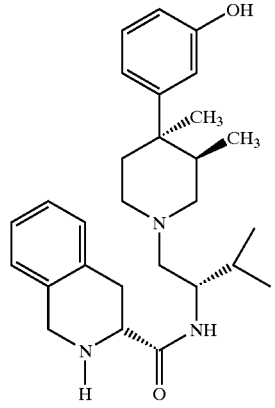

16

17

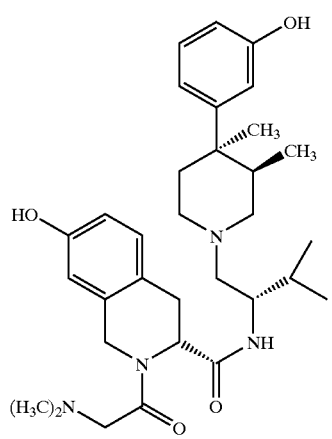

18

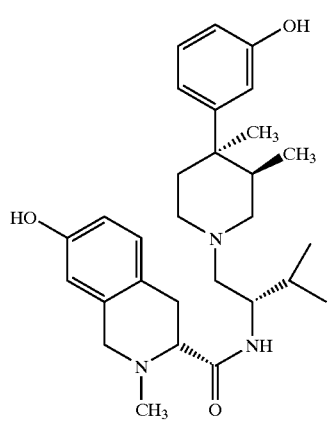

19

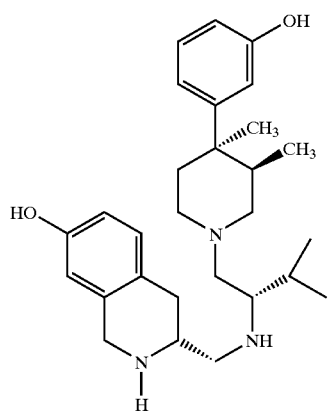

20

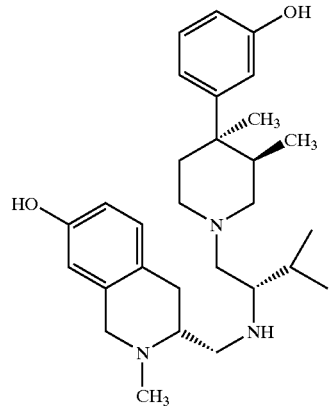

21

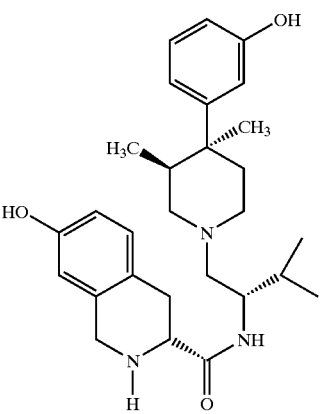

13. The pharmaceutical composition of claim 7, wherein said composition is an injectable composition.

14. The pharmaceutical composition of claim 7, wherein said composition is an orally administrable composition.

15. The pharmaceutical composition of claim 14, wherein said orally administrable composition is in a form selected from the group consisting of tablets, capsules, troches, powders, solutions, dispersions, emulsions and suspensions.

16. The kappa opioid receptor antagonist according to claim 1, having the chemical formula:

17

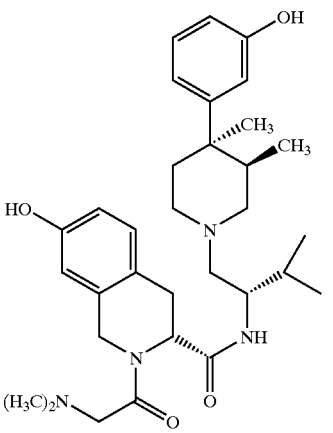

* * * * *

UNITED STATES PATENT AND TRADEMARK OFFICE
CERTIFICATE OF CORRECTION

PATENT NO.         : 6,974,824 B2                                    Page 1 of 1
APPLICATION NO. : 09/755021
DATED              : December 13, 2005
INVENTOR(S)        : F. Ivy Carroll It is certified that error appears in the above-identified patent and that said Letters Patent is hereby corrected as shown below:

Column 11, Line 60: Delete "$CH_2OR_3$ or $_{COCH2}$ $R_9$" and Insert --$CH_2OR_8$ or $COCH_2O_9$--

Column 17, Line 40: Delete "5 α" and insert --5α--

Column 20, Line 52: Delete "1H" and insert --11H--

Column 24, Line 44: Delete "Zimnerman" and insert --Zimmerman--

Column 24, Line 62: Delete "Wemer" and insert --Werner--

Column 33, Line 6: Delete "substitiients" and insert --substituents--

Column 34, Line 6: Delete "$NHR_{10}R_{11}$" and insert --$NR_{10}R_{11}$--

Column 45, Line 61: Delete "oploid" and insert --opiod--

Signed and Sealed this

Twenty-eighth Day of November, 2006

JON W. DUDAS
*Director of the United States Patent and Trademark Office*